(12) United States Patent
Chase

(10) Patent No.: US 12,128,214 B2
(45) Date of Patent: Oct. 29, 2024

(54) INTELLIGENT DRUG DELIVERY SYSTEM

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 0 days.

(21) Appl. No.: 17/314,306

(22) Filed: May 7, 2021

(65) Prior Publication Data

US 2021/0260284 A1 Aug. 26, 2021

Related U.S. Application Data

(63) Continuation-in-part of application No. 16/593,020, filed on Oct. 4, 2019, now Pat. No. 11,000,647.

(51) Int. Cl.
*A61M 5/172* (2006.01)
*A61B 5/00* (2006.01)
(Continued)

(52) U.S. Cl.
CPC ......... *A61M 5/1723* (2013.01); *A61B 5/1118* (2013.01); *A61B 5/4839* (2013.01); *A61M 5/14248* (2013.01); *A61M 5/172* (2013.01); *G06F 1/163* (2013.01); *G16H 20/17* (2018.01); *A61B 2562/0219* (2013.01);
(Continued)

(58) Field of Classification Search
CPC .................... A61M 5/172; A61M 2230/63
See application file for complete search history.

(56) References Cited

U.S. PATENT DOCUMENTS 5,987,352 A * 11/1999 Klein .................... A61N 1/375
600/509
6,094,598 A * 7/2000 Elsberry ........... A61M 5/14276
607/116
(Continued)

FOREIGN PATENT DOCUMENTS

CA 2896800 A1 7/2014
CN 1449840 A 10/2003
(Continued)

OTHER PUBLICATIONS

Holscher, C. Insulin, incretins and other growth factors as potential novel treatments for Alzheimer's and Parkinson's diseases. Biochem. Soc. Trans. (2014) 42, 593-599 (Year: 2014).*
(Continued)

*Primary Examiner* — Jenna Zhang
(74) *Attorney, Agent, or Firm* — McCormick, Paulding & Huber PLLC

(57) ABSTRACT

A controller and associated multi-axis sensor system for augmenting the automatic intelligent delivery of one or more drugs is provided. The controller and associated multi-axial sensor system are based on the detection and determination of particular physical lifestyle events. As a specific example, a pump augmentation system includes a six-axis accelerometer sensor, a gyroscopic pitch sensor and a controller. The controller is configured to receive motion data from the six-axis accelerometer sensor and orientation data from the gyroscopic pitch sensor. The controller provides a pump instruction signal for changing a delivery rate of a drug to a user based on the motion data and the orientation data. The system and methods are particularly suited for treating a user with Parkinson's disease.

27 Claims, 6 Drawing Sheets

(51) Int. Cl.
  *A61B 5/11* (2006.01)
  *A61M 5/142* (2006.01)
  *G06F 1/16* (2006.01)
  *G16H 20/17* (2018.01)

(52) U.S. Cl.
  CPC . *A61M 5/14244* (2013.01); *A61M 2205/3327* (2013.01); *A61M 2205/52* (2013.01); *A61M 2230/63* (2013.01)

(56) References Cited

U.S. PATENT DOCUMENTS

| | | | |
|---|---|---|---|
| 9,314,190 B1* | 4/2016 | Giuffrida | A61N 1/36003 |
| 2002/0072932 A1 | 6/2002 | Swamy | |
| 2007/0250134 A1* | 10/2007 | Miesel | A61N 1/36003 607/45 |
| 2008/0183060 A1 | 7/2008 | Steil et al. | |
| 2008/0195166 A1* | 8/2008 | Sun | A61B 5/4815 607/18 |
| 2008/0220092 A1* | 9/2008 | Dipierro | A61N 1/30 514/249 |
| 2010/0042043 A1 | 2/2010 | Krijnsen et al. | |
| 2010/0185181 A1 | 7/2010 | Alme et al. | |
| 2010/0265072 A1* | 10/2010 | Goetz | G16H 40/67 604/151 |
| 2011/0098676 A1* | 4/2011 | Chiang | A61P 25/24 604/512 |
| 2011/0124996 A1 | 5/2011 | Reinke et al. | |
| 2012/0143021 A1* | 6/2012 | Nagar | A61M 5/1723 600/301 |
| 2013/0245545 A1 | 9/2013 | Arnold et al. | |
| 2013/0274654 A1* | 10/2013 | Tsoukalis | A61M 5/142 604/67 |
| 2014/0323961 A1 | 10/2014 | Blomquist et al. | |
| 2016/0012749 A1* | 1/2016 | Connor | A61B 5/00 600/13 |
| 2016/0374597 A1* | 12/2016 | Stahmann | A61B 5/14503 600/309 |
| 2017/0091419 A1 | 3/2017 | Hoglund et al. | |
| 2017/0156662 A1* | 6/2017 | Goodall | A61B 5/7282 |
| 2018/0200433 A1* | 7/2018 | Cirit | A61M 5/1454 |
| 2019/0009019 A1* | 1/2019 | Shor | H03H 9/0585 |
| 2019/0192764 A1 | 6/2019 | Brewer et al. | |
| 2021/0100951 A1 | 4/2021 | Chase | |
| 2021/0100999 A1 | 4/2021 | Rosenbluth et al. | |

FOREIGN PATENT DOCUMENTS

| | | |
|---|---|---|
| CN | 1728154 A | 2/2006 |
| CN | 104067131 A | 9/2014 |
| CN | 105688308 A | 6/2016 |
| CN | 107073207 A | 8/2017 |
| JP | 2012502693 A | 2/2012 |
| JP | 2014519374 A | 8/2014 |
| JP | 2014204998 A | 10/2014 |
| WO | 2010031059 A2 | 3/2010 |
| WO | 2012153295 A2 | 11/2012 |
| WO | 2016110804 A1 | 7/2016 |

OTHER PUBLICATIONS

First Examination Report and its English translation for corresponding Indian Application No. 202247017957 dated Sep. 2, 2022.
International Search Report for corresponding PCT Application No. PCT/US22/39272 dated Nov. 1, 2022.
Extended European Search Report dated Sep. 1, 2023 for corresponding EP Application No. 208719161.
Japanese Office Action with its English translation dated May 30, 2023 for corresponding JP Application No. 2022-520802.
Chinese Office Action and its English translation dated Oct. 25, 2023 for corresponding CN Application No. 202080084214.5.

* cited by examiner

INTELLIGENT DRUG DELIVERY SYSTEM

CROSS-REFERENCE TO RELATED APPLICATION

This application is a continuation-in-part application of U.S. patent application Ser. No. 16/593,020, filed Oct. 4, 2019, which is hereby incorporated by reference in its entirety.

TECHNICAL FIELD

The present disclosure generally relates to a controller and associated sensor system based on lifestyle event detection, and more particularly relates to a controller and associated sensor system for augmenting the automatic delivery of drugs based on the detection and determination of particular lifestyle events (a Pump Augmentation System (PAS)). In one aspect, the controller and associated sensor system relates to the operation of insulin pumps, and more particularly relates to an Insulin Pump Augmentation System (IPAS) for assisting insulin pump delivery of insulin to a user based on lifestyle event detection. In another aspect, the controller and associated sensor system relate to an Intelligent Drug Delivery System (IDDS) for collecting patient motion information and providing a continuous medicinal infusion pump with patient motion feedback information in order to effectuate a closed-loop dosage determination.

BACKGROUND

Despite the progress of diabetic management via an insulin pump, even after the introduction and integration of continuous glucose monitoring with a "closed loop" approach, there still remains a disconnect between the capability of conventional insulin pump systems to satisfactorily detect and compensate for changing physiological, lifestyle, and exercise of an individual. All of these situations frequently result in unexpected raising and/or lowering of blood glucose levels, often times such that the blood glucose levels are outside of their desired, targeted or acceptable glucose ranges.

As an example, the everyday act of simply awakening for an individual triggers a release of hormones that characteristically causes a person's blood glucose level to rise. In a non-diabetic individual, the blood glucose levels are organically adjusted so these situations go unnoticed. In a diabetic individual, however, there is no (or only a limited) physiological mechanism that recognizes and compensates for such circumstances. Currently, treatment of diabetes generally relies on an "after the fact" corrective measures to bring the changing blood glucose levels back to normal ranges.

In contrast to the need to treat rising blood glucose levels, diabetic individuals also continually face the opposite problem, even with "closed-loop" insulin pump therapy. Normal physical activity such as working, walking, or exercising can frequently bring a diabetic individual's blood glucose level down to dangerously low levels. To complicate matters even further, in certain circumstances the same physical exertion during a period of elevated blood glucose levels can actually further increase the blood glucose levels to a dangerous degree.

At its core, the overall control problem results from the fact that insulin pumps follow a rigid, time of day based delivery process for the continuous, or basal, rate of insulin delivery, as well as only being able to react to an abnormal glucose level after a deviation has already occurred, or is in the process of taking place.

At its best, conventional insulin pumps or closed-loop insulin pumps are inherently limited to indirectly reacting to changes in interstitial fluid glucose levels, which are in of itself a delayed measure of true blood glucose levels. Present treatment methods lack the ability to dynamically and automatically proactively increase or decrease an insulin delivery rate, and therefore such methods merely treat the consequential effects of lifestyle or physiological activity.

Unlike many clinical treatments that are guided by empirical clinical measurements related to a patient's condition, Parkinson's disease does not have a defined laboratory test upon which to empirically judge either the progression of the disease and/or the true efficacy of treatments. As a result, a Parkinson's disease clinician is forced to depend on either a patient's subjective self-evaluation of a change in condition and/or observations made during a clinical snapshot of the patient in order to evaluate a patient's condition in an effort to determine whether a medicine dosage adjustment is necessary in an effort to minimize or curtail abnormal movement symptoms. Unfortunately, such methods for basing dosage adjustments typically result in dosages that are in excess of what is actually required, which in itself creates secondary complications.

The use of a conventional infusion pump to deliver Parkinson's disease related medication may offer limited benefits to a patient such as preventing missed doses and/or preventing inadvertent duplicate doses, but typically cannot be used to deliver medication doses when a patient is sleeping. Even with the use of a conventional infusion pump, there is still great clinical uncertainty as to whether the correct/optimum dosage has been determined, especially during sleep periods when a patient is unable to provide self-observations and not usually able to be observed in a clinical setting.

SUMMARY

According to a first aspect, a controller based on lifestyle event detection, and more particularly a controller for augmenting the automatic delivery of drugs based on the detection and determination of particular lifestyle events may be provided.

For example, in one embodiment, an insulin pump augmentation system may include a body, an accelerometer sensor, a gyroscopic pitch sensor, and a controller. The accelerometer sensor may be arranged on the body and configured to output motion data based on detected motion. The gyroscopic pitch sensor may be arranged on the body and configured to output orientation data based on detected orientation. The controller may be in communication with the accelerometer sensor and the gyroscopic pitch sensor. Further, the controller may be configured to receive the motion data and/or the orientation data. The controller may be configured to generate a pump instruction signal based on the motion data and/or the orientation data. The pump instruction signal may include a signal to change an insulin delivery rate of an insulin pump.

The signal to change an insulin delivery rate of an insulin pump may be a signal to reduce or increase the flow of insulin, to start a flow of insulin, to stop the flow of insulin, or to deliver an insulin bolus amount.

According to another embodiment, the controller may be configured to analyze the motion data and/or the orientation data on a time weighted basis. Further, the controller may be configured to utilize a data pattern matching algorithm to provide a determination of an occurrence of a lifestyle event of a user. The data pattern matching algorithm may utilize pattern data previously entered by a user. The pump instruction signal may be based, wholly or partly, on the determined lifestyle event.

The controller may also be configured to receive circulating insulin level data indicative of a level of insulin circulating within the user. The pump instruction may be based, wholly or partly, on the circulating insulin level data.

The controller may be configured to receive blood glucose level data indicative of a level of blood glucose level within the user. The pump instruction signal may be based, wholly or partly, on the blood glucose level data.

The controller may be configured to analyze the circulating insulin level data and the blood glucose level data. The pump instruction signal may be based, wholly or partly, on the analysis of the circulating insulin level data and the blood glucose level data.

According to another aspect, the controller may be configured to analyze the circulating insulin level data and the blood glucose level data with regard to the determined lifestyle event. The pump instruction signal may be based, wholly or partly, on the analysis of the circulating insulin level data and the blood glucose level data with regard to the determined lifestyle event.

According to a further embodiment, the controller may be configured to analyze the motion data and/or the orientation data on a time weighted basis. The controller may be configured to utilize a data pattern matching algorithm to compare the motion data with one or more predetermined motion data patterns stored in the pump augmentation system. The controller may further be configured to determine at least one of a type of food being ingested by the user, a quantity of said food being ingested by the user, and a resultant carbohydrate load being ingested by the user. The controller may be configured to determine a target amount of insulin based on at least one of the determined type of food, the determined quantity of food, and the determined carbohydrate load. The pump instruction signal may be based, wholly or partly, on the determined target amount of insulin.

According to another embodiment, the controller may include a memory and be configured to store in the memory the motion data and the orientation data received by the controller during a lifestyle event of a user. Further, the motion data and orientation data may be associated with a specific type of lifestyle event of a plurality of types of lifestyle events.

According to one embodiment, the insulin pump augmentation system may be incorporated within, and operationally connected to either an internal or external insulin pump which is attached to the user.

According to one embodiment, the body of the insulin pump augmentation system may be a stand-alone wearable device configured to be worn by the user. The wearable device may be configured to be worn on a limb, such as on the arm at the wrist of the user, and is operationally connected to either an internal or external insulin pump which is attached to the user.

According to another embodiment, the insulin pump augmentation system may include a microphone configured to detect audio and to output audio data based on the detected audio. The controller may be configured to receive the audio data. The pump instruction signal may be based, wholly or partly, on the audio data received by the controller.

According to even another embodiment, the controller may include a memory and be configured to store in the memory certain previously stored audio data received by the controller during ingestion of food. The controller may also be configured to receive an identifying input from the user to define and match a particular food type of the food previously ingested and matched to the audio data received by the controller. The controller may be configured to store the audio data in association with the particular food type indicated by the input. Further, the controller may be configured to determine a particular food type based on the stored audio data.

The controller may be configured to store, into a memory, the motion data and the orientation data received by the controller during a previous ingestion of a particular type of food. In the memory, the motion data and orientation data may be associated with a particular food type of a plurality of food types.

The controller may be configured to receive a selection from the user of physical ingestion characteristics of the particular food type based on stored motion data and orientation data or other physical ingestion characteristics.

According to an embodiment, the controller may be configured to select a particular food type from a plurality of food types, stored in a memory, based on at least one of the motion data, the orientation data and the audio data. The controller may further be configured to generate the pump instruction signal based on the selection of the particular food type.

The controller may be configured to estimate a quantity of calories ingested by a user and maintain a running caloric count representative of a sum of calories ingested by the user throughout a time period. Further, the controller may be configured to generate a signal when the sum of calories ingested by the user is greater than or equal to a predetermined caloric threshold.

The controller may be configured to estimate a quantity of carbohydrates ingested by a user and maintain a running carbohydrate count representative of a sum of carbohydrates ingested by the user throughout a time period. Further, the controller may be configured to generate a signal when the sum of carbohydrates ingested by the user is greater than or equal to a predetermined carbohydrate threshold.

According to another embodiment, the insulin pump augmentation system may include an indicator emitting device configured to emit a sound(s) or vibration. The controller may be operatively connected to the indicator emitting device and configured to increase the sound level and/or vibration level and increase a duration of the sound and/or vibration when the controller determines a user is non-responsive to acknowledging the sound or vibration.

The controller may be operatively connected to a communication device, and may be configured to cause the communication device to be activated when the controller determines the user is not responding to an escalating series of alarm sounds or vibration. Optionally, when the communication device is activated, an emergency call or message may be sent that includes real-time medical information relevant to the user and/or location information.

According to another aspect, a pump augmentation system may include a body, at least a six-axis accelerometer sensor, a gyroscopic pitch sensor, and a controller. The six-axis accelerometer sensor may be arranged in or on the body and configured to output motion data based on detected motion. The gyroscopic pitch sensor may be arranged in or on the body and configured to output orientation data based on detected orientation. The controller may be operatively connected to the six-axis accelerometer and the gyroscopic pitch sensor and configured to receive the motion data and/or the orientation data. The controller may be configured to generate a pump instruction signal based on the motion data and/or the orientation data, wherein the pump instruction signal may include a signal to change a material delivery rate of a pump.

According to another aspect, a method of augmenting a pump system includes monitoring motion data and/or orientation data, and generating a pump instruction signal based on the motion data and/or the orientation data. The pump instruction signal may include a signal to change a material delivery rate of a pump. The pump system may include a device body, an accelerometer sensor arranged in or on the device body and configured to output the motion data based on detected motion, a gyroscopic pitch sensor arranged in or on the body and configured to output the orientation data based on detected orientation, and a controller connected to the accelerometer and the gyroscopic pitch sensor, the controller being configured to receive the motion data and/or the orientation data. The controller may perform the generating a pump instruction signal.

According to another aspect, an intelligent drug delivery system (IDDS) and method uniquely provides an objective analysis of drug efficacy over time because the system can continuously monitor any physical symptoms that a patient presents and continuously analyze the effect of various dosages even while a patient is asleep and, therefore, incapable of making any subjective observations during a large portion of the day, e.g. one-third of the day.

An IDDS according to the present disclosure uniquely provides a way to quantitatively measure and evaluate a patient's symptoms through the patient wearing a sensing device of the IDDS on their wrist(s) and/or other parts of their body. The sensing device(s) may be used in a stand-alone manner for the purpose of supplying a physician with instant and/or archived empirical data for a clinician or physician to base subsequent dosage decisions for either oral or infusible medication. The sensing device(s) can be used with an operative connection to a continuous medical infusion pump to form a closed loop system.

These and other objects, features and advantages of the present invention will become apparent in light of the description of embodiments and features thereof, as illustrated and enhanced by the accompanying diagrams.

DETAILED DESCRIPTION

Figure 1:
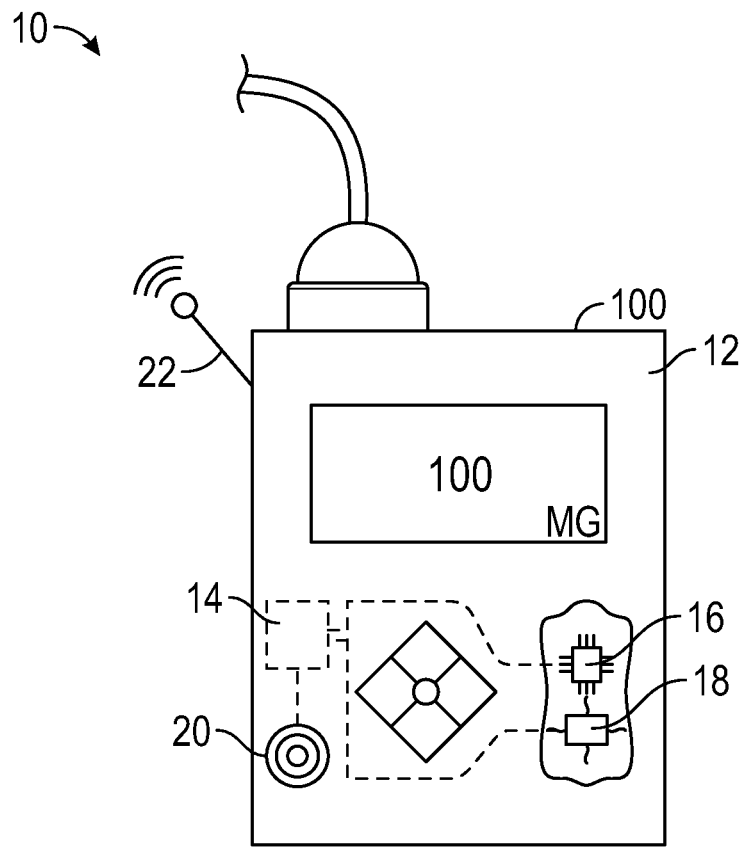
FIG. 1 shows an exemplary pump for a pump augmentation system (PAS) (e.g., an IPAS-enabled insulin pump or an IDDS-enabled drug delivery pump) in accordance with embodiments of the present disclosure.

Before various embodiments are described in further detail, it is to be understood that the present disclosure is not limited to the particular embodiments described. It will also be understood that the methods and apparatuses described herein may be adapted and modified as appropriate for the application being addressed and that the devices, systems and methods described herein may be employed in other suitable applications, and that such other additions and modifications will not depart from the scope thereof.

Although various features have been shown in different figures for simplicity, it should be readily apparent to one of skill in the art that the various features may be combined without departing from the scope of the present disclosure.

Certain features and elements of the Pump Augmentation Systems (PAS) described below are applicable to an Insulin Pump Augmentation System (IPAS) for treating diabetes and/or to an Intelligent Drug Delivery System (IDDS) for treating diseases such as Parkinson's disease. An IPAS is configured for delivering insulin, while an IDDS may be configured to deliver an anti-tremor medication or other medication for treating a patient with Parkinson's disease.

According to certain aspects, a controller associated with a Pump Augmentation System (PAS) or with an Insulin Pump Augmentation System (IPAS), in accordance with the present disclosure, provides improved pump operation or insulin pump operation control schemes and devices and systems for use with a pump or an insulin pump.

For example, the present disclosure provides an Insulin Pump Augmentation System (IPAS), which uniquely provides a closed-loop insulin pump with an understanding of various physiological and/or lifestyle activities its user is undergoing in real-time, so as to allow for dynamic proactive automatic compensation for said activities to better keep a diabetic individual's (or other individual) blood glucose level within a "desirable" target range. This proactivity is immensely important, as the mechanical insertion of insulin into a body, whether through a manual injection process or through an insulin pump, does not confer the same immediate glycemic response to a diabetic individual's glucose level, as compared to what a "normal" (non-diabetic) organic solution would provide.

There is a time lag between changes in blood glucose levels and when those changes are subsequently reflected by interstitial fluid readings, and as a result the existing "after the fact" insulin delivery reaction and correctional methods to external lifestyle factors typically result in undesirable "out of range" conditions. While insulin pumps are generally able to deliver different preset basal insulin infusion (delivery) rates based upon fixed, predetermined time schedules, these rates are not able to take into consideration the typical variations to an insulin pump user's varying schedule.

As an example, with the rise in glucose levels that diabetic individuals experience upon awakening as a result of the "Dawn Phenomenon," the best that current technology can do is to be statically programmed to allow for an increased basal insulin delivery during a specific pre-set time frame. The obvious problem with this method, however, is that unless an individual exactly conforms to the strict time schedule corresponding to the expected insulin delivery increase, this timed increased insulin delivery level will not match the actual glucose level insulin requirement, and can result in abnormally low or high blood glucose levels.

Given the reality of the numerous every-day "real-world" variations, precisely achieving both an exact time to bed, as well as an exact time of awakening in order to maintain consistent sleep durations in order to predict when a hormone release should occur is almost impossible to achieve consistently. Since present-design insulin pumps do not have the ability to recognize changes in sleep patterns (such as is experienced with variations between weekday sleep schedules and weekend or vacation sleep schedules, etc.), there is an inherent timing issue with the present treatment methods which prevent the proper response to the "Dawn Phenomenon" blood glucose changes.

In a similar fashion, conventional insulin pumps have no way to proactively react to spontaneous physical activity, whether it is during emergency situations (such as having to run down numerous flights of during an emergency evacuation), or for pleasure (such as a spontaneous extra round of tennis or other sporting activity that was not previously envisioned), and as a result even a closed-loop insulin pump crudely attempts to reactively reduce or suspend insulin delivery after the fact in order to maintain control.

Where 'conventional' (non-PAS enabled or non-IPAS-enabled) 'smart watches' or similar devices are capable of generating reports or saving information about the total number of strides or other physical activity, these devices only display prior information such as calories burned and distances covered, and are not configured for automatic responsive action based on such information for controlling or modifying an insulin pump. In contrast, according to an aspect of the present disclosure, a controller (for example, a controller integrated into an IPAS) uses sensed data to automatically determine and provide beneficial changes to the insulin delivery rate of an insulin pump (e.g. increases and/or decreases of insulin delivery rate). The novel use of an Insulin Pump Augmentation System (IPAS), which may, for example, incorporate one or more six-axis accelerometer/gyroscopic pitch sensors (or other number of axis accelerometer(s)), and whose data output may be processed and analyzed in real-time through an artificial intelligence software program, for the first time gives a closed-loop insulin pump the ability to have physiological and/or physical situation awareness in order to better match insulin delivery levels to a body's actual insulin requirements. IPAS is also ideally suited for common problematic situations, where insulin-pump users either forget to temporarily suspend the insulin delivery of their pump beforehand and/or during exercise, and/or forget to bolus for a planned or ingested carbohydrate load. Both aforementioned situations can result in potentially serious blood-glucose excursions developing, which may be avoided through the use of IPAS according to embodiments of the present disclosure.

For the purposes of present disclosure, the term "lifestyle" includes events such as: a person's current sleep state (e.g., determining if a person is awake or sleeping); a person's current exercise or physical motion state (or movement state); a person's current food intake state (eating, chewing, drinking, etc.); and a person's real-time identification of a specific food currently being ingested as well as the total quantity of that food having been ingested. A "lifestyle" situation awareness augmentation provided to an insulin-pump by an IPAS allows a closed-loop insulin pump to monitor and automatically correct for physical exertion activity which may change a user's glucose level, a 'real-time' monitoring, identification, and insulin compensation for a range of ingested food, and the ability to monitor an individual's sleep/awake status and compensate for end-of-sleep hormone release changes to a user's blood glucose level.

According to certain aspects, a controller is associated with an Insulin Pump Augmentation System (IPAS). An IPAS can be configured in different physical embodiments, with three exemplary embodiments including:

1) IPAS components being completely integrated into the body of an IPAS-enabled insulin pump. The data from the pump's integrated IPAS sensors being processed by an associated Artificial Intelligence sub-system within the IPAS, and the resultant guidance being provided to the insulin pump's delivery system(s) to act upon (or a controller of the insulin pump delivery system(s)).

2) The configuration of embodiment #1, further augmented by the additional use of a physically separate second six-axis accelerometer and gyroscopic pitch sensor, and a microphone that is integrated into a wrist-worn device that is placed on an insulin-pump user's arm or wrist (preferably the dominant arm or wrist), either as an IPAS-enabled smart-watch or as a proprietary IPAS wearable device. The data output from these additional sensors is transmitted to an IPAS-equipped insulin pump (e.g. through wireless communication means), where the added data stream is combined with the data supplied from the pump's integral sensor(s), with both data streams subsequently being processed by an Artificial Intelligence sub-system within the insulin pump.

3) A configuration for use with a non-IPAS enabled closed-loop insulin pump. In this configuration, all of the IPAS sensing elements as well as the IPAS data processing functions are physically integrated into the body of a "smart-watch" or other IPAS wearable device which is worn on the wrist or arm of an insulin pump user (e.g. the dominant wrist or arm). An integral six-axis accelerometer and gyroscopic pitch sensor, along with a microphone are used as input devices. In this embodiment, the IPAS-enabled arm-worn device itself calculates supplemental insulin and/or delivery modification instructions, and then wirelessly transmits said instructions to a 'conventional' insulin pump, i.e. non-IPAS equipped insulin pump, for execution. Said insulin pump would also transmit "real-time" parameters such as blood-glucose levels and circulating insulin to the IPAS device.

In a first example of what the newly-found lifestyle awareness conveys to an insulin pump, the augmented pump will now be capable of dynamically determining a sleep state or an awakened state of a user, and proactively make compensating adjustments to an insulin delivery rate commensurate with an estimated body's release of hormones upon awakening. With this new lifestyle awareness, the glucose lowering effect of insulin can now be better timed to match the escalating blood-glucose effects of a hormone release upon awakening with a commensurate insulin release upon the IPAS sensing the physically awakened state of an insulin-pump user.

In accordance with embodiments of the present disclosure, a controller associated with an IPAS may determine that an individual is in a sleeping state or non-sleeping state based on the individual's physical orientation. For example, whether said individual is physically oriented in a position characteristic of sleep along with a reduced state of motion for an extended period of time, an IPAS, through its six-axis accelerometer(s) and gyroscopic pitch sensor(s) can similarly recognize the physical positioning and a long-term lack of motion of an individual, and match this data with a stored template indicative of a sleeping state for that individual. Conversely, when the controller associated with the IPAS detects that an individual has changed from a limited motion, long duration sleeping state position to an upright position through detected multi-axis motion, then a determination of a non-sleeping state position (or awakening state or morning awakening) by the IPAS can also be made. The IPAS Artificial Intelligence subsystem can determine through an algorithm that, for example, includes a time-weighted motion analysis (to prevent short duration awakening from being incorrectly interpreted as morning awakening), as well as observing the range and speed of detected motion, in order to filter out the typical transient movement and position shifting of an individual during various sleep phases from an actual awake state.

With the inherent ability of the controller associated with the IPAS to detect the sleeping state of a user, IPAS has the capability to not only advance or delay the pre-programmed time-based basal rates, but it can also correct and align the fixed/preset basal rates with actually observed conditions such as is encountered when sleeping or travelling between time zones. Similarly, an IPAS according to embodiments of the present disclosure can temporarily skew a current basal rate to better align with instant or predicted near future bodily insulin requirements.

An IPAS's sleep/awake determination can also provide critical user-condition determination and responses. In the instance of the controller associated with an IPAS-equipped insulin pump sensing an abnormally low (or excessively high) blood glucose reading while its user is presumed sleeping, it can both increase the volume levels of a warning alarm(s), as well as the duration of such alarms beyond its usual daytime parameters, as arousing a sleeping person experiencing low blood-glucose levels can be especially challenging. In some embodiments, in the event that an IPAS-equipped insulin pump, after the completion of an enhanced alarm sequence(s) does not sense an awakened condition, the controller associated with the IPAS is configured to presume that the user has lost consciousness (or is otherwise non-responsive) and automatically commands a nearby mobile device to place an emergency call for medical help. Simultaneously, the controller associated with the IPAS may cause an insulin pump to automatically suspend insulin delivery. In the event of a non-responsive individual along with an observed extremely low blood-glucose indication, IPAS may be configured to automatically suspend insulin delivery and/or deliver an infusion of glucose-raising medication such as Glucagon. In the case of excessively high blood glucose levels, IPAS may be configured to automatically deliver an appropriate insulin bolus to avoid or correct a ketonic situation. For example, the controller associated with the IPAS could command the nearby mobile device through Bluetooth wireless communication or the like. Even though the unconscious individual may be unable to speak, a digitized voice message would indicate to an emergency operator the nature of the medical emergency, as well as relay the location of the user through GPS or other location information technology of the mobile device should that information not be available via enhanced 911 systems. Optionally, IPAS could deliver to the emergency operator the observed blood-glucose levels for more timely situation awareness and action by first responders.

In a second example, a non-IPAS enabled insulin pump is completely ignorant as to the 'moment to moment' lifestyle activities of its user, and thus has no ability to proactively deviate from its preset delivery settings. It is well known that physical activity affects a diabetic individual's blood glucose levels, either by lowering a diabetic individual's blood-glucose level or raising it depending on what the blood glucose level is at the time of said exercise. By the use of an integrated multi-axis accelerometer and pitch sensing sensor (or separate adjunct multi-axis accelerometer and gyroscopic pitch sensors), an insulin pump is able to gain a continuous (or semi-continuous) insight into a user's exercise/physical activity, and dynamically and proactively adjust the user's insulin delivery rate accordingly, rather than attempting to reactively correct a resultant change in blood glucose level as accomplished through conventional insulin pump devices.

According to embodiments of the present disclosure, an IPAS may achieve improvements in a user's "in-range" glucose readings. Changes in exercise or physical activity can now be immediately detected (or nearly immediately) allowing for contemporaneous alteration to a user's basal insulin rate immediately (or near immediately) upon the initiation of exercise. Artificial Intelligence (A.I.) logic may be employed to both analyze a user's current blood-glucose levels as well as determine the (presently) circulating insulin levels (as provided by the insulin pump) to make appropriate insulin adjustments by the pump as needed. If the instantaneous circulating insulin level at the time of exercise is deemed adequate and the detected blood glucose level is within a 'normal' range (or within a predetermined range), then the controller associated with the IPAS may be configured to bias the insulin pump to stop or lower the insulin delivery basal rate commensurate with the sensed level and duration of exercise. If at the time of exercise commencement, the detected blood glucose level is well above normal (or is above a predetermined threshold) and/or there is a low level of circulating insulin (or is below a predetermined threshold), then the controller associated with the IPAS may be configured to cause the insulin pump to either bolus and/or increase its basal rate to compensate for the exercise so as to prevent a further increase in blood glucose levels caused by the exercise.

A determination of exercise or other strenuous activities (such as playing tennis) may be made through an A.I. motion algorithm, which may base the determination on how many active axes are reporting motion above a predetermined motion threshold level, the excursion ranges of said reporting axes, and any repeating cadence patterns (to detect running or other specific activities). The algorithm may be designed to filter out 'false' exercise reporting situations, such as when an individual is riding in a car (repeated rising up and down) so as not to confuse said vertical 'bouncing' up and down with the vertical motions one might associate with running. The motion algorithm would note that while there were vertical (and potentially other motions), the excursion distances were limited from what one would expect from exercise, with forward movements and other axis readings missing along with a very different cadence pattern.

The Insulin Pump Augmentation System (IPAS) is not limited to the lifestyle examples described herein. Conventional insulin pumps have no direct means for lifestyle awareness, and as a result of this deficiency, the pump is completely unaware of a user's food ingestion. Without a "real-time" method to sense an ingested carbohydrate load, conventional closed-loop pumps are oblivious to food being ingested, and merely indirectly and reactively sense that the user's blood glucose levels are rising toward or beyond a target range or rate before initiating corrective action. Even in the case where an insulin-pump user manually boluses insulin prior to food consumption, this action is just a guess as to how much carbohydrate may or may not subsequently get consumed.

With the present invention, an IPAS-equipped insulin pump is not only contemporaneously presented with real-time information indicative of food ingestion, but in many cases, even the precise type of food, the actual quantity of food consumed, the resultant calculated ingested carbohydrate load, the glycemic index of said food, and a compensating insulin bolus amount and release timing for that ingestion may be estimated and provided to the pump. This allows an insulin pump to immediately (or near immediately) and contemporaneously proactively match supplemental insulin dosages to the amount as well as type of food being consumed, as opposed to a non IPAS-equipped pump needing to reactively compensate for said food ingestion in an imperfect "after the fact" manner.

As an example, in the case of a person eating popcorn, the dominant hand (or non-dominant hand) wearing an IPAS sensor(s) repeatedly moves in a distinct pattern while taking food from a fixed "supply container" and bringing the popcorn to their mouth. By analyzing the data from one or more of the six-axis accelerometer sensors and/or one or more of the gyroscopic pitch/yaw/roll sensors during this activity, a distinctive repetition pattern allows the controller (for example, with an incorporated A.I. algorithm) to record the detected arm and hand movements, which can be accurately saved as a template representative of that particular food being ingested. The controller/A.I. system may not only analyze the repeated multi-axial positional locations, speed, and cadence of said movements, but it may also generate a digitized audio file from the wrist-mounted microphone when the wrist worn device is determined to be at the closest position to the mouth of the user. The audio file may further assist the A.I. algorithm in differentiating between, for example, a person eating popcorn and a person eating potato chips by differentiating between their distinctive chewing sounds, as well as the duration of chewing sounds.

By determining and analyzing the "linger" time that a hand is held at or near a mouth, as well as the number and type of sequential angular movements of the hand and wrists before moving away from the mouth, this allows a further quantitative determination of what has been ingested, and by supplemental simple calculation, the instantaneous carbohydrate ingestion level for each such movement cycle may be calculated, and a determination as to a compensatory insulin "bolus" is made. By infusing insulin proximate (and at the appropriate compensating level) to ingestion taking place, as tempered by the glycemic index of the identified food, a superior proactive match of insulin and carbohydrate load may be made.

The variation in types of foods is quite extensive. By having an individual "record" various foods being eaten, as well as data labeling of the recorded foods, a controller associated with an IPAS according to embodiments of the present disclosure can easily match and reference the carbohydrate value, the glycemic index, calories, etc. to precisely tailor the delivery values necessary for an insulin pump to match the insulin need and timing to compensate for a glucose level increase in the blood caused by that food when ingested.

The physical motions and cadences typically associated with eating various foods can be quite distinctive for certain foods. Examples of this include, without limitation, the eating an ear of corn, the eating an apple (with distinctive 'snap back' after each bite), the licking of an ice cream cone, the peeling and eating of a banana, etc. Because of unique physical movements while eating and/or eating sounds associated with each food, a series of specialized food templates may be generated and/or pre-stored in the controller associated with the IPAS. Additionally, manually inputting the food type into the IPAS by a user, for example by pressing a button on the wrist-worn device and speaking the name of a particular food, the carbohydrate and caloric information may be recalled (or identified) for foods that have difficulty in being automatically recognized based on a food template, and the IPAS will monitor the ingestion amount to resolve (or determine) a carbohydrate load and insulin bolus. For low-carbohydrate food such as meat, the IPAS may recognize the unique motions of meat cutting before ingesting (if the user prepares the food for ingestion).

The sound characteristics of not only the actual ingestion of a beverage, but also the sounds (or lack of) created by the actual bottle or container may be especially important in identifying what the beverage (and its carbohydrate content) is. For example, disposable plastic water bottles, since they do not need to handle the pressures of carbonation, are typically constructed of much thinner plastic material than 'soda' bottles, and as such they produce a characteristically unique "plastic flexing/crackling" sound when handled and being consumed from. This unique plastic water bottle sound would be used by IPAS to determine that a non-caloric/zero carbohydrate ingestion was taking place. Conversely, a carbonated beverage would use a different type of bottle as well as producing different ingestion/carbonation sounds. With regard to determining whether the carbonated beverage is "diet" or regular (with their corresponding vastly different carbohydrate amounts), the IPAS algorithm merely needs to analyze the user's blood glucose level at the time of ingestion to make a logical differentiation. Since an IPAS user is presumed to be a diabetic, then unless the user's glucose level was low at the time of ingestion (which would make the ingestion of a "regular" soda or the like desirable in that situation), then the beverage is always assumed to be "diet".

Every food when ingested has a unique combination of positional and rotational presentations to the mouth, a distinct biting pattern and sound, juice sucking sounds, chewing noises, hand retraction rotation and positioning, etc.

In some embodiments, the controller associated with the IPAS may not directly identify a type of food based on a pre-stored food template, but rather using a matching process wherein individual food templates are recorded and saved by the user during ingestion, with the user then manually identifying and registering each different food. Subsequent food identification may be accomplished by the IPAS automatically comparing in real-time active food ingestion with the saved digital motion and sound patterns of the saved templates. When a match is made, the carbohydrate levels, glycemic indices, caloric information, and other information is provided to the insulin delivery system for determining insulin delivery amount(s) and timing of said delivery amount(s).

The algorithm that the controller associated with the IPAS used to determine ingested food types may incorporate one or more validation methods to increase accuracy. One of these methods is to only allow food audio matching (as captured by the wrist-worn device) during periods when the IPAS motion analysis determines that a user's hand is in a position proximate to their mouth. By the use of such 'audio gating', the IPAS may prevent false analysis when multiple people are eating either the same type, or other food types in close proximity to the subject IPAS. Said audio gating also inherently provides a level of privacy due to the wrist microphone being muted whenever the system does not detect a hand being raised and brought proximate to the mouth. Accordingly, the IPAS may not record audio data from the microphone when the IPAS is determined to not be at a proximate position to a mouth of the IPAS user, or disregard the recorded audio data if the IPAS is recording the audio data.

In some embodiments, the controller associated with the IPAS is configured to initially contain a number of 'generic' motion templates to immediately allow for recognition of awakening, running, or other activity. The IPAS is configured to not only allow a user to generate and replace said 'generic' templates with their own custom individualized templates to further increase both event recognition and accuracy, but also to supplement the range of stored templates. The custom personalized templates may also replace the generic motion templates or be used in addition thereto for recognition of awakening, running, or other activity.

Another benefit of a controller associated with an IPAS according to embodiments of the present disclosure comes into play during episodes of hypoglycemia. In some circumstances, individuals typically over-compensate their carbohydrate ingestion to treat the immediate symptoms of hypoglycemia. In some embodiments, the IPAS is configured to monitor an instant blood-glucose level, the amount of circulating insulin, as well as the amount of carbohydrate being ingested. The controller associated with the IPAS may be configured to provide the user with an 'overshoot' protection alert to guard against excessive carbohydrate ingestion subsequently resulting in hyperglycemia. By the IPAS comparing said ingestion against both the instant glucose level as well as the amount of circulating insulin, it can calculate (or determine) the appropriate amount of carbohydrate needed to normalize the user's blood-glucose level by monitoring the instant carbohydrate ingestion and sound an alert at a point of over-compensation.

In some embodiments, the controller may be associated with a Pump Augmented System (PAS). The PAS may also be used for delivery of other infusible medications or other infusible materials, such as, for example and without limitation, medications for treating Parkinson's disease. In this usage example, infused medication delivery time(s) and amount(s) can be matched with an instant need, as determined, for example, by an increased tremor level which a PAS would detect.

For the purposes of the present disclosure, while the primary disclosed application is for the augmentation of an insulin pump, the same or similar hardware configuration, with minor software modification, may also be used for other purposes. In a further embodiment of the controller, the automatic food ingestion sensing may also be used as an 'ingestion' caloric monitor as opposed to current devices that only report calories that were 'burned', rather than consumed. In some embodiments, a controller configured for caloric ingestion monitoring may optionally be configured to provide tactile or visual alarms or other guidance notification once a target caloric ingestion has been achieved or failed to be achieved by a certain time of day.

The present disclosure provides a controller associated with a system for sensing and determining "lifestyle" activities.

Figure 2:
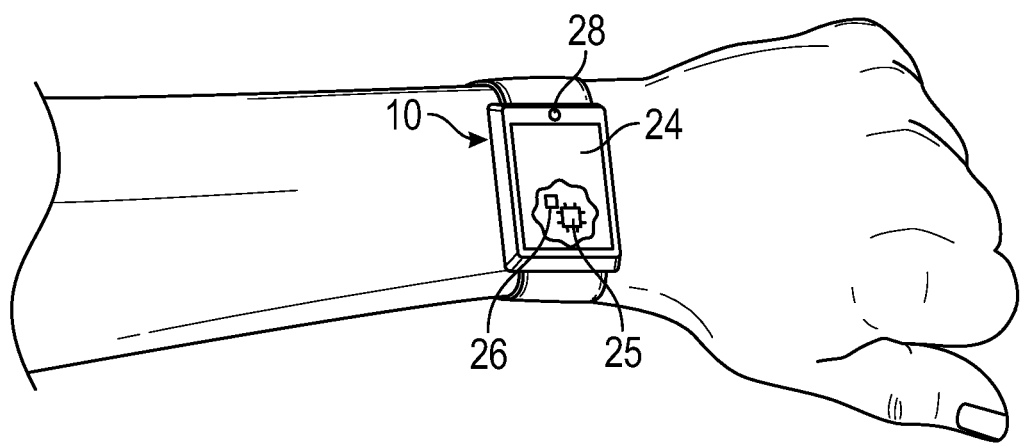
FIG. 2 shows an exemplary PAS-enabled wrist-worn device (e.g., an IPAS-enabled wrist-worn device or an IDDS-enabled wrist-worn device) in accordance with embodiments of the present disclosure.

According to the present disclosure a Pump Augmentation System (PAS) 10 for sensing and determining "lifestyle" activities of a drug delivery pump user is provided. Referring to FIGS. 1 and 2, the PAS 10 could be specifically implemented as an Insulin Pump Augmentation System (IPAS) or as an Intelligent Drug Delivery System (IDDS).

According to certain specific embodiments, an Insulin Pump Augmentation System (IPAS) for sensing and determining "lifestyle" activities of an insulin pump user is provided. As shown in FIG. 1, the Insulin Pump Augmentation System 10 in accordance with embodiments of the present disclosure is integrated into, and/or operatively in communication with a drug delivery pump, such as an insulin pump, 100 having a pump body 12. The IPAS 10 includes a controller 14, an accelerometer sensor 16, a gyroscopic pitch sensor 18, an indicator emitting device 20 and a transmitter 22. The accelerometer sensor may be a multi-axis accelerometer sensor, for example, a six-axis accelerometer sensor.

The controller 14 is operatively connected to the six-axis accelerometer sensor 16, the gyroscopic pitch sensor 18, the indicator emitting device 20 and the transmitter 22. While the controller 14 is shown as being physically connected to the six-axis accelerometer sensor 16, the gyroscopic pitch sensor 18, the indicator emitting device 20 and the transmitter 22, the controller 14 may be "connected" to these elements through wireless communication methods and connections.

The six-axis accelerometer sensor 16 is configured to detect motion (or movement) and output motion data (or movement data). The controller 14 is configured to receive and/or record or store the motion data from the six-axis accelerometer sensor 16. The gyroscopic pitch sensor 18 is configured to detect orientation and output orientation data. The controller 14 is configured to receive and/or record the orientation data from the gyroscopic pitch sensor 18. The indicator emitting device 20 is configured to emit one or more sounds (for example, an alarm sound) at various sound levels and/or to display one or more visual indicators (for example, a flashing light). The controller 14 is operatively connected to the indicator emitting device 20. The transmitter 22 is configured to communication with one or more communication devices.

The controller 14 is configured to communicate with the insulin pump 100 and receive various insulin pump 100 data. For example, and without limitation, the controller 14 may receive circulating insulin level data of a user of the insulin pump 100, a reported blood glucose level data of the user of the insulin pump 100 and/or a current or scheduled insulin delivery rate data of the insulin pump 100. The controller 14 is operatively connected with a host insulin pump 100. The controller 14 is also operatively connected to the transmitter 22 to cause the transmitter 22 to trigger an automatic emergency call or message if one or more predetermined criteria is satisfied based on the motion data, orientation data, audio data, circulating insulin level data, reported blood glucose level data and/or current or scheduled insulin delivery rate data.

As shown in FIG. 2, the IPAS 10 is further integrated into, and/or operatively in communication with a wearable device 24. In this embodiment, the wearable device 24 is a wrist worn device. The IPAS 10 includes a six-axis accelerometer sensor 25 and gyroscopic pitch sensor 26 located in the wearable device 24. The IPAS 20 further contains a microphone 28. The microphone 28 is configured to detect audio and output audio data. The controller 14 is configured to receive the audio data from the microphone 28 and/or the wearable device 24 includes an additional controller(s) which is configured to distribute the motion data, orientation data and/or audio data to the controller 14. It should be readily understood that the microphone 28 may be arranged in other positions of the wearable device 24 and/or there be additional microphones.

In some embodiments, the controller 14 is arranged in or on the wearable device 24. In some embodiments the controller 14 is arranged in or on the insulin pump 100 as shown in FIG. 1, and a second controller is arranged in or on the wearable device 24. The second controller being configured to communicate with the first controller 14 and/or a dedicated controller of the insulin pump 100.

Figure 3:
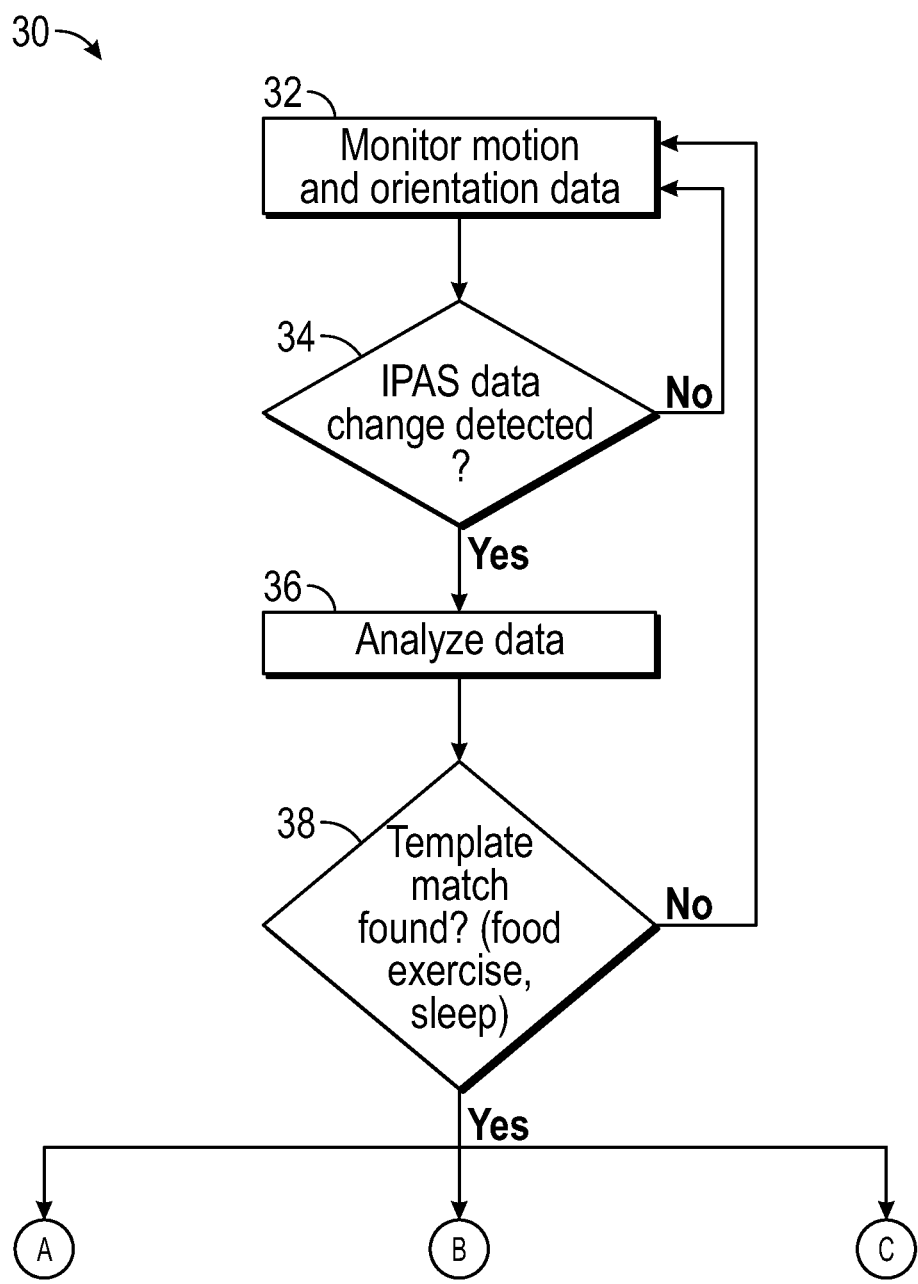
FIG. 3 shows an exemplary flow diagram for the operation of the IPAS of FIG. 1 in accordance with embodiments of the present disclosure.

Referring to FIG. 3, a flow diagram 30 shows an exemplary method of operation of the IPAS 10 of FIG. 1 in accordance with embodiments of the present disclosure. At block 32, the controller 14 monitors for motion data received from one or more of the six-axis accelerometer sensors 16, 25 and for orientation data from one or more of the gyroscopic pitch sensors 18, 26. At block 34, the controller 14 determines if the motion data and/or orientation data has changed. If the controller 14 determines that there is no change in the motion data and/or orientation data, then the controller 14 returns to block 32 for monitoring. If the controller 14 determines there is a change in the motion data and/or orientation data, the controller 14 proceeds to block 36 where the change in motion data and orientation data is analyzed by the controller 14. The controller 14 proceeds to block 38 where the controller 14 compares the motion data and orientation data, which may be time-weighted, for similarities with a profile template stored in the IPAS 10. If the controller 14 determines that the motion data and/or orientation data is not similar to a stored profile template, the controller 14 returns to block 32 for monitoring. If the controller 14 determines that the motion data and/or orientation data is similar to a stored template, the controller 14 determines that the motion and orientation detected is associated with the ingestion of food and proceeds to the identified profile template method.

Figure 4:
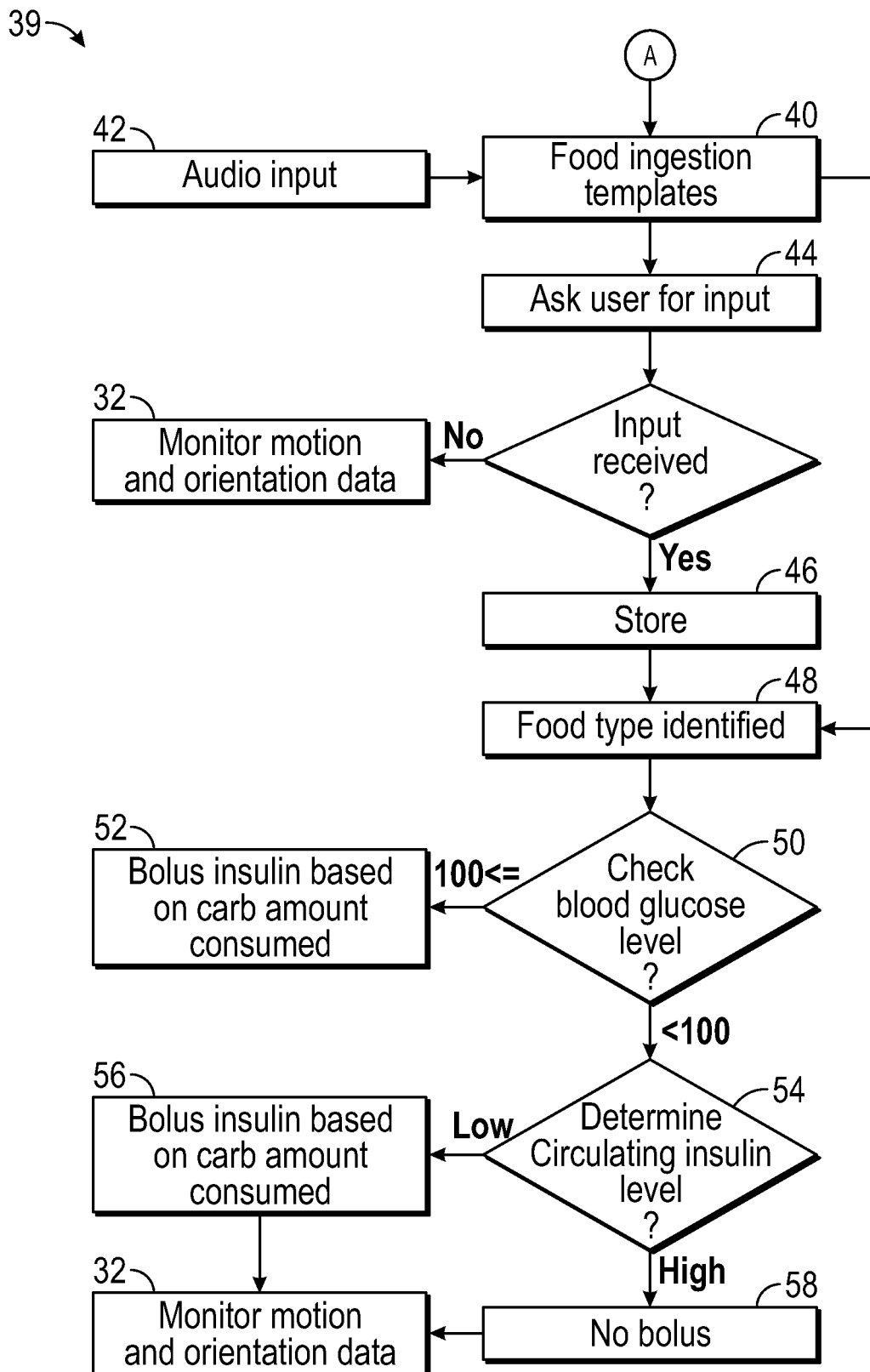
FIG. 4 shows an exemplary flow diagram for the operation of the IPAS of FIG. 1 in accordance with embodiments of the present disclosure.

Referring to FIG. 4, a flow diagram 39 shows an exemplary profile template method of operation of the IPAS 10 of FIG. 1 when the motion data and/or orientation data is determined as being similar to a food ingestion profile at block 38 (FIG. 3) in accordance with embodiments of the present disclosure. The controller 14 proceeds to block 40, where the controller 14 optionally receives audio input 42 from the microphone 28 (FIG. 2). The controller 14 compares the motion data, orientation data and/or audio data corresponding to the time period determined to be contemporaneous with ingestion of food for a similarity with one or more stored food ingestion templates. If the controller 14 determines that the data is similar to a stored food ingestion template, the controller proceeds to block 48, which is discussed in greater detail later herein. If the controller 14 determines that the data is not similar to a stored food ingestion template, the controller proceeds to block 44 and requests user input for food type of food being ingested. If no user input is received, the controller 14 returns to block 32 for monitoring. If user input is received, the controller 14 proceeds to block 46 and stores the motion data, orientation data and/or audio data as corresponding to a new food ingestion template of the input provided. The new food ingestion template is stored (e.g. in a memory associated with the controller) for future food ingestion template comparisons at block 40. Then the controller 14 proceeds to block 48.

At block 48, the controller 14 determines a particular food type identified as being indicative of the food being ingested by the user. The controller 14 proceeds to block 50 where the controller 14 checks for a reported blood glucose level of the user (e.g. by querying the insulin pump 100). If the reported blood glucose level is greater than or equal to a predetermined threshold (e.g. 100 mg/dl), then the controller 14 generates a pump instruction signal at block 52 causing the insulin pump 100 to bolus insulin to the user based on the amount of carbohydrate load ingested (or consumed) as determined by the controller 14, thereby changing the current or scheduled insulin delivery rate of the insulin pump 100. If the reported blood glucose level is less than a predetermined threshold (e.g. 100 mg/dl), then at block 54 the controller 14 checks a circulating insulin level within the user (e.g. by querying the insulin pump 100). If the circulating insulin level is below a predetermined threshold, at block 56 the controller 14 generates a pump instruction signal to bolus insulin to the user based on the amount of carbohydrate load ingested (or consumed) as determined by the controller 14. If the circulating insulin level is above a predetermined threshold, then at block 58, the controller 14 does not generate a pump instruction signal or generates a pump instruction signal that reduces the insulin delivery rate from the current or scheduled insulin delivery rate. Then the controller 14 returns to block 32 for monitoring.

Advantageously, the controller 14 being configured to request and receive input from a user at blocks 44, 46 allows the controller 14 to repeatedly learn the physical characteristics and/or mannerisms unique to the user. The stored patterns are individualized to the user allowing the controller 14 to identify food templates (or other templates) more accurately. The controller 14 may be configured to store any number of templates input by the user giving the controller 14 the ability to store virtually infinite patterns unique to the user. The ability to store patterns unique to the user advantageously allows for the controller 14 to "learn" the user tendencies (or previously entered pattern data) that correspond to a food template (or other template). For example, a user may tend to generate one or more unique motions, orientations or sounds when engaging in a physical lifestyle event that the controller 14 can identify as a particular template once stored. Thus, when the user again engages in that lifestyle event, such as eating potato chips in a particular physical manner, the controller 14 is configured to identify the lifestyle event and generate a pump instruction signal accordingly as disclosed herein.

Figure 5:
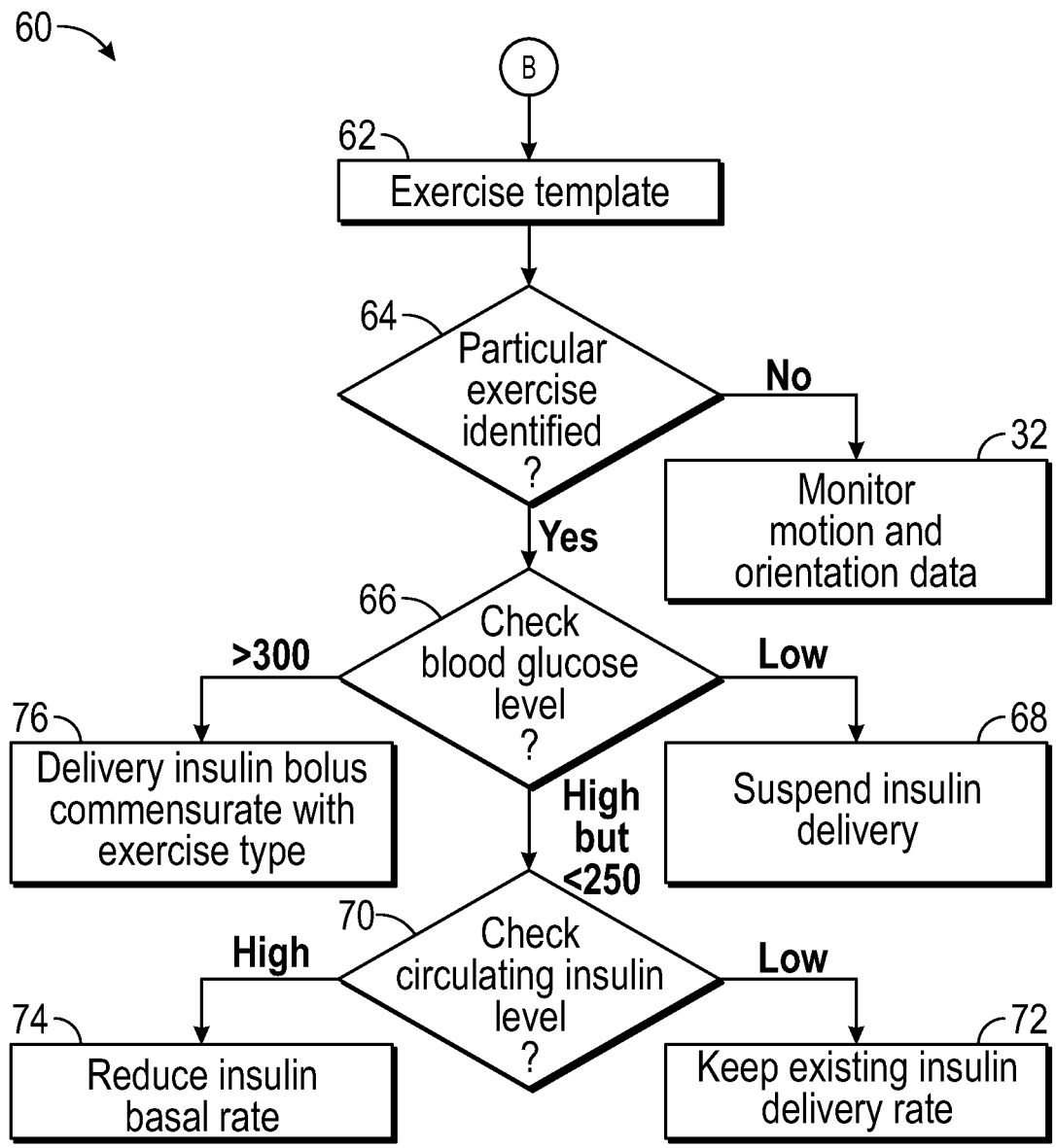
FIG. 5 shows an exemplary flow diagram for the operation of the IPAS of FIG. 1 in accordance with embodiments of the present disclosure.

Referring to FIG. 5, a flow diagram 60 shows an exemplary method of operation of the IPAS 10 of FIG. 1 when the motion and/or orientation data is determined as being similar to an exercise profile at block 38 (FIG. 3) in accordance with embodiments of the present disclosure. At block 62, the controller 14 compares the motion data and/or orientation data for similarity with a particular exercise profile. At block 64, if the controller 14 determines that the motion data and/or orientation data does not correspond to a particular exercise profile, then the controller 14 returns to block 32 monitoring. If the controller 14 determines the data does correspond to a particular exercise profile, the controller 14 proceeds to block 66 where the controller 14 checks for a reported blood glucose level. If the reported blood glucose level is below a first threshold, the controller 14 proceeds to block 68 and generates a pump instruction signal instructing the insulin pump 100 to suspend insulin delivery or decrease insulin delivery. If the reported blood glucose level is above the first threshold but below a second threshold (e.g. 250 mg/dl), the controller 14 proceeds to block 70 and checks a circulating insulin level within the user. If the circulating insulin level is below a first insulin threshold, the controller 14 proceeds to block 72 and maintains the existing insulin delivery rate (or at least does not cause the insulin delivery rate to change significantly). If the circulating insulin level is above a second insulin threshold, the controller proceeds to block 74 and reduces the insulin basal rate. Referring back to block 66, if the blood glucose level is greater than a third threshold, the controller 14 proceeds to block 76 and determines an increase in an insulin delivery rate and/or an insulin bolus commensurate with the particular exercise profile, the controller 14 generates a pump instruction signal to cause the insulin pump 100 to deliver the determined commensurate insulin rate or bolus.

Similar to the method discussed above in connection with FIG. 4, the controller 14 may be configured to request that the user enter an exercise template to be stored as corresponding to a recorded exercise profile. In some embodiments, the controller 14 does not need to request that the user enter an exercise or food template. The user can enter the corresponding template even when not requested by the controller 14. The entered template is stored with recorded data from the IPAS 10. In some embodiments the recorded data stored as the template corresponds to the data recorded during a predetermined amount of time before the entering of the template by the user, for example and without limitation, one minute, two minutes or three minutes. In some embodiments, the user can choose which recorded data is associated with the entered template. For example, the user can choose the amount of time prior to the entering of the template, or the user can choose a period of recorded data that occurred earlier in the day, e.g. if the user played tennis from 1:00 PM to 2:00 PM, later that day at 6:00 PM when the user is not playing tennis, the user could choose the time playing tennis as being stored as the tennis exercise profile or template.

Figure 6:
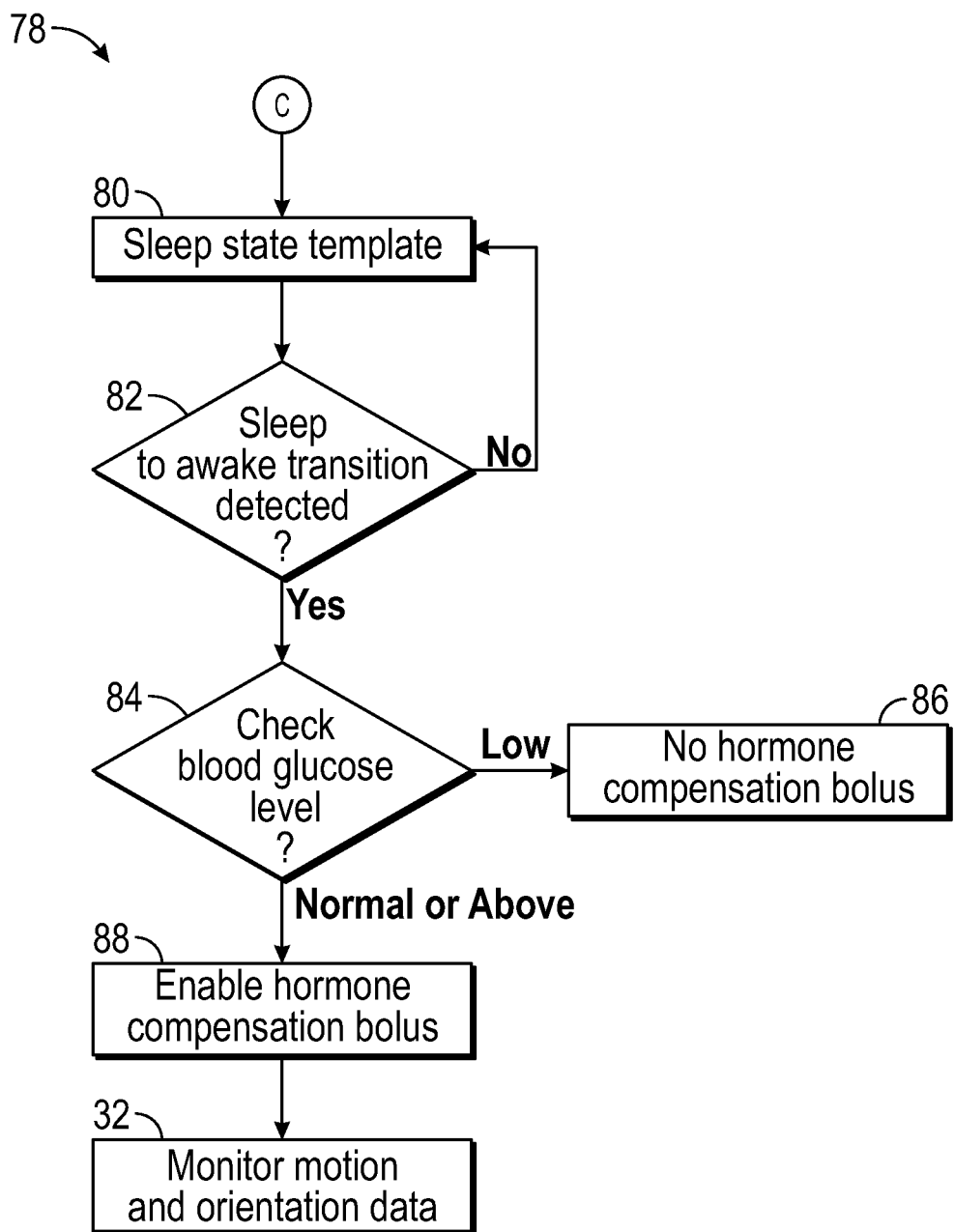
FIG. 6 shows an exemplary flow diagram for the operation of the IPAS of FIG. 1 in accordance with embodiments of the present disclosure.

Referring to FIG. 6, a flow diagram 78 shows an exemplary method of operation of the IPAS 10 of FIG. 1 when the motion and/or orientation data is determined as being similar to a sleep profile at block 38 (FIG. 3) in accordance with embodiments of the present disclosure. At block 80, the controller 14 determines a sleep state is detected. The controller 14 proceeds to block 82, where the controller 14 continues to monitor the motion data and/or orientation data for a determination of a sleep to awake transition, which may be based on a time-weighted evaluation of the data. If no sleep to awake transition is detected, the controller returns to block 80 to check the data is similar to a sleep profile and, if in the sleep state, returns to block 82 for determining if a sleep to awake transition has occurred. If the controller 14, determines that a sleep to awake transition has occurred (e.g. by the motion data indicating that the user is moving or walking, or the orientation data indicating that the orientation the IPAS 10 has changed), then the controller 14 proceeds to block 84 to check for a reported blood glucose level of the user. If the reported blood glucose level is below a first threshold, the controller 14 proceeds to block 86 where the controller 14 determines that no insulin bolus is necessary to compensate for hormone release associated with a transition to an awakened state as discussed herein. If the reported blood glucose level is above a second threshold, the controller 14 proceeds to block 88 where the controller 14 determines an increase in an insulin delivery rate and/or an insulin bolus to compensate for the user hormone release, then the controller 14 generates a pump instruction signal to cause the insulin pump 100 to release the appropriate insulin at the appropriate delivery rate. Then the controller 14 returns to block 32 for monitoring.

In some embodiments, an IPAS 10 is located entirely in or on an insulin pump 100 (e.g. FIG. 1). In some embodiments, an IPAS 10 is located in or on an insulin pump 100 and in or on a wearable device(s) 24 (e.g. FIGS. 1 and 2) and, as disclosed herein, the IPAS 10 elements in the wearable device 24 are configured to communicate and work with the IPAS 10 elements in the insulin pump 100. In some embodiments, an IPAS 10 is located entirely in or on a wearable device 24 (e.g. FIG. 2) and is configured to communicate and work with a non-integrated IPAS insulin pump (i.e. does not have any IPAS functionality by itself), where the IPAS 10 in the wearable device 24 supplements or overrides at least some control of the non-integrated IPAS insulin pump functions so that the insulin pump operates like an integrated IPAS insulin pump. In some embodiments, a user might wear one or more wearable devices containing IPAS 10 elements, for example and without limitation, a wearable device on each wrist of the user.

Advantageously, IPAS enabled pumps are configured to provide advantages over non-IPAS enabled pumps. For example, without an IPAS providing an insulin pump a real-time indication of a user's sleep status, a conventional insulin pump may generate unnecessary alarms without regard to context. As an example, some insulin pumps may keep track of the amount of remaining insulin in its reservoir, and at various insulin remaining levels the pump may sound an alarm indicating the situation. As a result of this, insulin pump users are often awoken to take certain actions such as to change reservoirs even though the situation is not yet critical and such actions are ill-advised to be done when just woken up in the middle of the night. In some embodiments, an IPAS enabled insulin pump may determine whether a user is sleeping, and, if an alarm is determined as being merely advisory rather than time or situation-critical, the IPAS enabled insulin pump may delay such alarms and/or notifications until the user is awake and/or until the status of the alarm becomes time-critical.

Features and elements of the PAS and IPASs 10 described above are applicable to an intelligent drug delivery system (IDDS) 10 for treating diseases such as Parkinson's disease and, therefore, will not be repeated in detail here. Instead of delivering insulin, an IDDS (or PAS) may be configured to alter the delivery rate of an anti-tremor medication or other medication for treating a patient with Parkinson's disease.

Quantitative measurable factors are not available for Parkinson's disease as are available for other diseases, such as glucose level, blood oxygen concentration level, blood pressure reading, EKG reading, body temperature, etc. Parkinson's disease differs in that there is no direct and continuous measurable universal reference values upon which to alter medicine delivery rates. Clinicians typically judge the progression of the disease based on visual observation(s) of a patient, and make subjective dosage changes therein.

The motion and/or orientation data collected by the IDDS device 10 is analyzed by the controller 14 to determine the presence of even subtle changes in physical movement symptoms. A high resolution Micro-Electromechanical Sensor(s) (MEMS) of the IDDS 10, e.g. six-axis motion tracking device which may include a three-axis gyroscope with a three-axis accelerometer, which allows for fine resolution detection of patient motions, which include tremor symptoms. Such resolution provides for accurate pitch, roll and yaw motion sensing capability in addition to the traditional three Cartesian coordinate axis measurements. Thus, an IDDS 10 device according to the present disclosure is configured, for instance, to monitor motions of a wrist/hand that is in a resting (or fixed) position having an X/Y/Z axis position, but whose fingers are rhythmically active, which are detected by the sensor(s) of the device 10, indicating a tremor incident of a detectable intensity and duration that may be recorded and stored in a local or remote storage. Embodiments using more advanced or higher resolution sensors may also be used.

With the use of a body-worn or internal to a medication pump sensor, the device 10 may be configured to differentiate from a normal upright position and a prone resting/sleeping position.

Each Parkinson's disease patient has individualized physical and/or cadence tremor characteristics throughout each stage of the disease. Thus, the ability to record and store tremor incidents allows for the comparison of motion for determining whether there is a change in duration and/or intensity of tremors, either increases or decreases, beyond a predetermined threshold, e.g. an increase of 10% duration or an increase of 25% force of tremor movements. In some embodiments, a device 10 is worn on each wrist of the patient (and/or a device 10 on one or more ankles of the patient). In some embodiments, a device 10 is worn on a general body location, such as on the torso.

A closed loop IDDS in operation with a patient, such as for treating a patient with Parkinson's disease, is configured to utilize the at least one body worn (e.g. wrist and/or general body location) motion and orientation sensor to operationally supplement or completely replace conventional infusion rate settings used by conventional non-intelligent continuous fusion pumps (e.g. fixed dosage delivery or particular time of day delivery infusion rate settings).

The term "continuous" as it is used in the context of the present disclosure will be understood by those of skill in the art to not literally mean drug delivery on a non-stop basis, but a continual repetition of delivery doses, with the spacing between dosing and the duration of each dose being dosage variables. In a similar fashion, it may not be advantageous to make observations of the patient literally every second as this non-stop observation may not provide significantly more data benefits as compared to data sampling with some length of time between data collection.

Advantageously, IDDSs allow for an infusion pump to provide dynamic timing and delivery rate adjustment settings of medication infusion flow rate(s) based on real-time observation of presented Parkinson's Disease symptom intensity levels. IDDSs according to the present disclosure may be configured to continually monitor, analyze, and adjust the basal rate of infusion pump medication in response to observed patient motion feedback. The observation may include monitoring body tremors, Dystonia, Dyskinesia, gait, and/or freezing as detected by one or more six-axis motion sensors.

Since each Parkinson's Disease patient throughout each stage of symptoms may have individualized physical and/or cadence tremor characteristics, an advantageous feature of IDDSs according to the present disclosure is the periodic recording and subsequent periodic matching and analysis between earlier individualized patterns and present patterns to determine if pattern excursions have changed in any metric (e.g. intensity, duration, type of motion, etc.). In some embodiments, an IDDS may function through a single wrist-worn sensor, typically on the body side presenting the greatest or more frequent abnormal symptoms. In some embodiments, an IDDS may function through two sensors, one on a wrist of the patient and one body worn for a greater number of data collection points that communicates with the controller of the infusion pump to make a determinations regarding pharmacological delivery rate changes based on the data from one or both sensor controllers. In some embodiments, an IDDS may function through a wrist-worn sensors and an additional body worn sensor for even more data collection points, e.g. a sensor that is worn around the waist or torso of the user (such as a sensor that comprises a belt or attaches to a belt). Various combinations of sensor numbers and locations may be used. In some embodiments, the drug infusion pump unit of the IDDS may have an integrated gyroscopic and/or orientation position sensor to provide positional information and/or to supplement the data from other sensors.

The controller 14 may be configured to analyze body movements attributed to a "base" or starting point movement level, and from this base level determination a pharmacological delivery rate is initially established/stored by the controller 14 with the movement data obtained from the one or more worn sensors through sensor input channels of the controller 14. By analyzing this data, the controller 14 is configured to generate an individualized baseline pharmacological delivery rate. A baseline deviation ratio is selected which applies a percent rate change to the pharmacological delivery rate (or other rate change, e.g. absolute volume rate change) to either increase or decrease the delivery amount based on sensed excursion position changes detected by the one or more worn sensors. Sensed positional data may normally be recorded and stored while the user is in a resting position to better filter out "noise" from the relevant positional data input channels. The controller 14 may analyze a subset of the data input channels for subsequent comparisons. Nevertheless, the system would continue to monitor all input channels (and non-relevant movement) in order to equalize the overall body movement context and prevent unnecessary data "noise" or influence.

The recording/analytical comparison interval periods may be selected by a clinician to reflect a meaningful or useful diagnostic comparison period. However, the controller 14 may be configured to delay any recordings/analysis until the overall body movement context is determined to be the same as during a previous recording. This delay would prevent data external to the body positional motion from falsely skewing the data collected.

In some embodiments, the IDDS is configured to determine whether a movement delta exists between a hand-worn sensor and a non-hand worn sensor (or reference sensor) on certain data input channels. By utilizing one or more non-wrist-worn six-axis sensors (such as one that may be integrated into the pump itself) to compare against a wrist-worn sensor, this would provide useful "external" (to a wrist-worn sensor) positional information and would be used to null or filter out any external to the body movement "noise", such as a person bouncing up and down while traveling in a car. If the same data input channels from both a wrist-worn sensor and a non-wrist sensor were detecting the same or similar data, the system or controller 14 would be able to determine that the data was not being created by the body itself and, thus, should not be attributed to a tremor. If just a wrist-worn sensor was sensing certain movement data without a "check" sensor also supplying positional data, there would not be a way to determine whether sensed body movement was separate from any external movement applied to the user and thus the detected movement would always be validly considered organic movement generated by the user.

In addition to random abnormal body movements (which would be recorded), one of the most common Parkinson's Disease symptoms is a constant tremor. A constant tremor is a rhythmical movement typical in each individual with Parkinson's Disease and may have an individual distinctive cadence. The individual distinctive cadence may be identified by the controller 14 through repeated detections of the movement or by manual calibration and identification by the user or clinician in the IDDS, and the IDDS is configured to record its existence. By empirically matching an instant comparison of the excursion limits of movements containing this cadence movement with a reference recording, a reliable measure of the progression of Parkinson's disease may be established. Any recorded and stored cadence examples also serve to filter the desired cadence movement information from normal lifestyle movement data that does not contain a known repetition rate to avoid extraneous data "noise."

Timely reporting of movement changes to a clinician is of substantial importance as it may indicate a needed change in dosage level or medication brand or type. An advantageous aspect to IDDS embodiments according to the present disclosure is the inclusion of outgoing data reporting capability. In other words, the IDDS is configured to communicate with a clinician computer system through wired or wireless communication means. For example, the IDDS may be configured to wirelessly connect with a cell phone of the user and cause the cell phone to transmit a message through cellular or internet network(s) to a clinician computer system. This allows the IDDS controller 14 upon sensing a continuing excessive (i.e. "out of range") abnormality to automatically contact a clinician. In some embodiments, the message to the clinician computer system may be to merely communicate a report of the detected excessive changes to the clinician. However, in some embodiments, the IDDS has the added ability to be remotely adjusted so a clinician may make an immediate dosage change(s) during or after any reporting session. The IDDS communications capability may include the use of WI-FI, cellular, or other communications methods or protocols in common use.

An IDDS according to the present disclosure may also have the capability to autonomously make dosage changes, to either increase or decrease, in response to detected symptomatic changes. The changes would be analyzed by the controller 14, for instance, on the basis of a patient exceeding a preset level of instant or averaged abnormal excursion increases, on the basis of exceeding a preset level of abnormal excursion decreases, a time of day context, etc. The range of automatic dosage delivery changes would be limited by a pre-set dosage (change) "collar" restraint with such autonomous limits determined by the clinician for each user.

Advantageously, an IDDS may be configured to continuously (or at desired intervals) record relevant data, make periodic comparisons between that data and previous data records, and/or take action upon the detection of physiological significant data changes. The comparisons may include individual sequential recording comparisons, or an averaging and comparison between timely groups of recordings.

In embodiments according to the present disclosure, the generation and storage of data readings for later analysis and action goes beyond the recording of "simple" or "raw" motion data. For example, an IDDS may use linked "metadata", or data that links the primary motion data values within context of other values which brings sub-context to the main data. This allows, for instance, the historical "raw" motion data to be directly linked to additional information such as time/date stamps, the pharmacological delivery rate at the time of recording, the estimated circulating medicine level at the time of recording, the medication type, the medication strength, the body activity level at the time of recording, the sleep/awake state at the time of recording, etc. This allows the associated physical body movement data to provide a much more meaningful and rich context. With such metadata, extensive reports, charts, and detailed analyses may be automatically generated for each patient, thereby creating a far more useful dynamic picture of dosage efficacy, etc. for each user/patient on an individualized level.

In some embodiments, an IDDS contains Artificial Intelligence (AI) which learns from the recording analysis of a user/patient relative to the results of prior automatic dose correction actions. The system's motion and orientation sensor(s), in addition to monitoring abnormal body movements also function as a lifestyle input sensor(s) to determine whether a person is sleeping, exercising, etc. Since individuals spend the majority of their day in an upright position whether standing, sitting, etc., the IDDS controller 14 assumes that this is the normal lifestyle position to differentiate against to determine whether a body is in a prone or resting/sleeping position.

As its name implies, IDDS is an intelligent drug delivery system that is capable of learning when and if various lifestyle conditions need dosage alterations to occur. Based on the analysis of a patient's historic reaction (or lack of a reaction) to certain level changes of infused medication, an IDDS is capable of reporting to a patient's clinician which dosage change(s) resulted in the most desirable balance between mitigation of symptoms and occurrence of side effects, and what minimum infusion rate(s) were required to achieve the desired changes for this balance to occur at.

A determination of a specific lifestyle event change would bias the automatic pharmacological delivery adjustment algorithm(s) to allow for appropriate remedial actions such as providing a non-planned medication rate increase should the IDDS detect, for instance, a user awakening from sleep, or reducing a medication basal rate should the IDDS detect the user falling asleep, etc. The lifestyle detection also plays an important role so as not to confuse the artificial intelligence, for instance, between sensing a reduction in physical symptoms caused by a medicine's resultant therapeutic action and a user sleeping with its inherent abnormal movement reduction typical of natural sleep paralysis. While people are typically creatures of habit and generally go to sleep about the same time each day, there are numerous outside factors and circumstances that can alter their schedule and dynamically require a dosage change to occur. An IDDS overcomes the time of day limitations of a conventional/non-intelligent continuous infusion pumps dosing rate schedule by allowing the IDDS to intelligently and dynamically base an instant dosage rate change by reacting to real-time sensing and lifestyle event determination. If a selected periodic recording time was reached and there was a data-skewing short-term lifestyle event taking place (e.g., exercising) the system would automatically enter a "try again later" mode which would delay and prevent any atypical recording or analysis, for instance, for a predetermined amount of time (e.g. 15 minutes or whatever time frame is determined to be appropriate by the controller's artificial intelligence or selected from a preconfigured amount of time selections).

An IDDS according to the present disclosure generates extended historical sensor recorded data, from which dosage "cause and effect" record data is stored within the IDDS pump controller 14 itself (or other memory). The IDDS allows the data to be able to be remotely accessed at any time by one or more medical professionals for the purpose of both clinically analyzing historic results, as well as allowing a post-analysis IDDS dosage change to be made remotely by a physician/clinician. This feature is especially important for patients located in areas remote to medical care, as well as overcoming the progressive inability of many Parkinson disease patients to be able to travel to a clinical setting. Even with clinical evaluations there is typically a progressive cognitive decline with Parkinson's disease patients that results in patients increasingly being unable to either observe their own true medical condition and/or adequately respond to medical questioning by a clinician. With an IDDS this problem is addressed by having most or all of the relevant data able to be completely accessible in an empirical fashion from among the stored data.

By continually monitoring a patient's movements, an IDDS is capable of noticing and analyzing any clinically relevant changes in movement excursions on an absolute basis, which for the first time allows a truly objective determination of Parkinson's disease progression to be made for any given time frame. An IDDS can also monitor on an absolute empirical basis the systemic and physiological effects of exercise, certain therapies, etc. on a patient so as to truly gauge what therapeutic efforts are working effectively or not.

An IDDS also uniquely provides new opportunities for clinicians to perform proactive range-bound medication changes in order to precisely and efficiently observe real-world cause and effect studies to determine the optimal dosaging for each patient. For example, an IDDS may be configured to do automatic dosage bracketing of pharmacologicals to empirically ascertain an optimum dosage level(s). For a given time period, which is selectable by a clinician, the IDDS will bias the overall dosing by a selectable percentage above or below a current baseline. For example, the IDDS would skew the average dosing a selectable step lower and then make an analysis of any resultant abnormal movement symptoms presented during the altered/skewed dosage period and compare the data results to the prior baseline. If the symptoms have generally stayed the same, the system would again repeat the stepped dosage reduction and continue with this until an increase in presented symptoms are noted and then return to the most recent previous dosage levels. The automatic bracketing may also be used in the opposite dosing direction to determine if there is symptom reduction with a higher dosage regime. Although the previous example was directed to an overall daily dosage study, an IDDS is also capable of automatic bracketing and analysis of just specific times of the day and/or days of the week. Since the metadata recorded by the IDDS includes the type/brand or analog information of the medication that was being infused (e.g. either inputted by the user or the clinician), it is relatively simple to conduct relative efficacy comparisons on an individual patient (or for that matter a group of patients) to empirically determine which of the available medications provide the best/most desired results as measured, for instance, by the total number of recorded abnormal movements within the same time frame and relative dosage for each medication. Similarly, an IDDS is a valuable platform for the empirical field-trial results of new Parkinson's medications as well.

Advantageously, since the actual infusion pump as well as the motion sensors are designed to run on battery power, medication infusion as well as tremor monitoring are able to continue despite commercial power outages or while traveling.

At times when the medication reservoir and infusion set are being changed, with one or more system components being taken offline to be recharged, etc., the infusion pump and/or the controller 14 would note this activity and either exclude any medication delivery logging information from that time period's recorded data, or annotate the data from that time period via metadata so as not to falsely skew the subsequent recorded data analysis.

At times when a body worn sensor is not being worn or the data from a device is otherwise unavailable (e.g. the sensor is undergoing a battery replacement or recharge, etc.) the controller 14 (or infusion pump controller) would discontinue its dynamic delivery rate determination method and instead proceed/continue with the last known dynamic infusion rate(s). During periods of extended loss of sensor data, the IDDS may operate in accordance with self-generated historical time-contextual infusion rates generated via recent pump activity. In the event the pump has not had sufficient operating activity such as in the case with a new pump, the system may operate in accordance with various traditional time of day non-dynamic dosage patterns that are typically based upon and altered strictly according to a daily time schedule so as not to allow a complete diminishment of circulating medication to occur. The IDDS would typically include a processor with an integral real time clock built into the system or functional equivalent.

In some embodiments, each IDDS component are serialized to ensure multiple sensors in a given area are uniquely linked to the appropriate serialized infusion pump, which would ensure data from a body worn sensor(s) is not mistakenly provided to a nearby infusion pump of a different user.

In some embodiments, the infusion pump of an IDDS allows for the release of both an active pharmacological medication as well as an adjunctive precursor medication (agonist) that IDDS would automatically and appropriately infuse prior to the infusion of the primary pharmacological agent.

In some embodiments, the IDDS continually calculates the level of circulating Levodopa (or other pharmacological agent) at any given time with said calculation based on the infusion timing and dosing levels of the pharmacological agent and attaches that circulation level as metadata. Additionally, the IDDS tracks and records the peak and minimum circulating levels of said pharmacological for any given time frame in order to be able to retroactively analyze these levels against the sensed abnormal movements such as tremors, freezing onset, dystonia, Gait abnormalities, and/or dyskinesia in the same time frame in order to further clinical evaluation. This essentially eliminates the need for a patient to maintain a "motor diary" which is of limited value relative to IDDS in that it cannot provide critical details such as the circulating level of a pharmaceutical during each episode or for any given time.

In some embodiments, an overall goal of the IDDS is to provide an optimized level of medication that minimizes or curtails instant tremors or other body motion abnormalities. In the context of Parkinson's Disease control, an optimized level of medication provides for just the minimum level of daily medication infusion that is consistent with abnormal motion control in order to avoid over-medicating the patient. Without dynamic dosing control, it is inevitable that excess medication dosaging will occur at times, along with times of sub-optimal medication levels. This results in "off" periods wherein insufficient pharmacological levels cause a lack of abnormal movement control. Without a dynamic control of pharmacological levels as provided by IDDS, inevitably there are numerous times when the pharmacological levels are much higher than are necessary, with this hyper-dosing causing further complications such as the onset of dyskinesia.

A body worn sensor may be adhesively attached to a body in order to ensure the sensor orientation is indicative of a certain body orientation.

IDDS may also include an ambient light sensor to further aid in the detection of a lifestyle event such as sleeping.

The use of a wireless charging grid that may be an integral part of a blanket, bed-sheet, etc. may allow wireless charging of the controller and/or body sensors.

The IDDS controller may employ Digital Signal Processing (DSP) in its determination of position and/or acceleration data results.

IDDS provides for dosage delivered feedback from a infusion pump to the controller.

Figure 7:
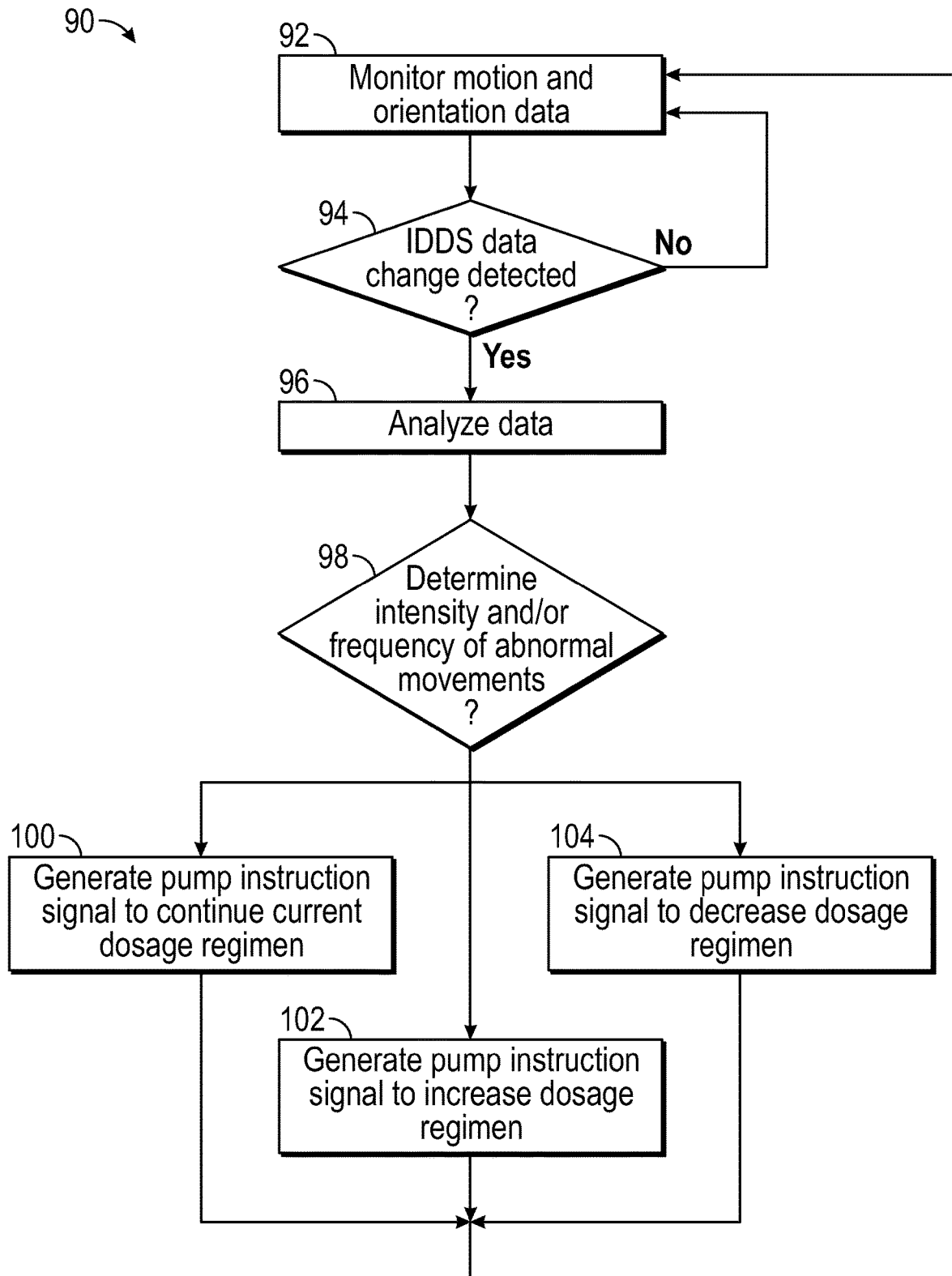
FIG. 7 shows an exemplary flow diagram for the operation of the IDDS of FIGS. 1 and 2 in accordance with embodiments of the present disclosure.

Referring to FIG. 7, a flow diagram 90 shows an exemplary method of operation of the IDDS of FIGS. 1 and 2 in accordance with embodiments of the present disclosure. At block 92, the controller 14 monitors for motion data received from one or more of the six-axis accelerometer sensors 16, 25 and for orientation data from one or more of the pitch sensors 18, 26. At block 94, the controller 14 determines if motion data and/or orientation data has changed. If the controller 14 determines that there is no change in the motion data and/or orientation data, then the controller 14 returns to block 92 for monitoring. If the controller 14 determines there is a change in motion data and/or orientation data, the controller 14 proceeds to block 96 where the change in motion data and/or orientation data is analyzed by the controller 14. The controller 14 proceeds to block 98 where the controller 14 compares the motion data and orientation data, which may be time-weighted, with previously recorded motion data and orientation data of the user associated with abnormal behavior movements (or tremor incidents) or compares the data with other baseline data, in order to determine an intensity and/or frequency of abnormal movements. If the controller 14 determines that the intensity and/or frequency of the abnormal movements are within a predetermined threshold and/or have not changed by a predetermined amount (or percentage) from previous data of the user (or baseline data) then the controller 14 determines that the current dosage regimen of the current pharmacological drug should be maintained and the controller 14 proceeds to block 100. At block 100, the controller 14 generates a pump instruction signal to continue or maintain the current dosage regimen, e.g. by maintaining the current delivery rate of the pharmacological drug.

If the controller 14 determines that the intensity and/or frequency is above a predetermined threshold, or if the intensity and/or frequency has increased from previous data (or other baseline data) beyond a predetermined amount (or percentage), then the controller 14 determines that the dosage regimen needs to be increased and the controller 14 proceeds to block 102. At block 102, the controller 14 generates a pump instruction signal to increase the dosage regimen, e.g. by increasing the current delivery rate of the pharmacological drug.

If the controller 14 determines that the intensity and/or frequency is below a predetermined threshold, or if the intensity and/or frequency has decreased from previous data (or other baseline data) beyond a predetermined amount (or percentage), then the controller 14 determines that the dosage regimen may be decreased or that it is an appropriate time to perform dosage bracketing and the controller 14 proceeds to block 104. At block 104, the controller 14 generates a pump instruction signal to decrease the dosage regimen and/or perform bracketing, e.g. by decreasing the current delivery rate of the pharmacological drug.

Following blocks 100, 102 and 104, the controller 14 proceeds to monitoring motion and orientation data at block 92 in order to repeat the above described process or to perform dosage bracketing as discussed above.

An advantage of IDDSs according to the present disclosure is the ability to provide long-term recording storage, and analysis of data involving the relationship between observed abnormal body movements within the context of historical medication dose(s) that was delivered to a patient in order to precisely observe the instantaneous dosage requirements of a patient with the historically delivered medication rate(s) of an infusion pump while also tracking and observing any trending progression of the disease.

In certain embodiments, the motion sensors of an IPAS enabled insulin pump serve as an adjunct to the direct continuous measurement of a trackable value (e.g. blood glucose) to augment the insulin pump delivery rate in response to the existence of a "Lifestyle" event while in some embodiments the motion sensors in an IDDS serve as the primary means of controlling the delivery rate of medication.

The foregoing description of embodiments of the present disclosure has been presented for the purpose of illustration and description. It is not intended to be exhaustive or to limit the invention to the form disclosed. While the exemplary application has focused on the treatment of Parkinson's disease, with minor programming and/or hardware modification, both the monitoring and closed-loop capability of IDDS may also be used with other neurological conditions and treatment, thus obvious modifications and variations are possible in light of the above disclosure and should be considered to be within the scope and spirit of the present disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. An intelligent drug delivery system comprising:
   a device body;
   an accelerometer sensor arranged in or on the device body and configured to output multi-axis motion data based on detected multi-axis motion and acceleration;
   a gyroscopic pitch sensor arranged in or on the device body and configured to output orientation data based on detected orientation;
   a controller in communication with the accelerometer sensor and the gyroscopic pitch sensor, the controller being arranged to be worn by a user;
   wherein, based on the multi-axis motion data and/or the orientation data, the controller is configured to determine positional movements of the device body, a multi-axial speed and acceleration of movement of the device body, linger times of the device body, and/or a multi-axial cadence of movement of the device body;
   wherein the controller is configured to generate a pump instruction signal based on the determined multi-axial movement of the device body, multi-axial speed and acceleration of the device body, the linger times of the device body, and/or the multi-axial cadence of movement of the device body, the pump instruction signal including an instruction to change or suspend a delivery rate of a pharmacological material to achieve a daily dosage of the pharmacological material;
   wherein the pharmacological material is configured to treat one or more abnormal movement symptoms of Parkinson's disease; and
   wherein the controller is configured to autonomously dynamically determine whether adjustment to the daily dosage is needed and autonomously dynamically adjust the daily dosage in a closed-loop manner between the sensors arranged in or on the device body and the controller, without input of a dosage change, based on a current physically detected Parkinson's disease symptom intensity level or range of the user determined by the controller in order to optimize the daily dosage to achieve a minimum level consistent with abnormal motion control of the user.

2. The intelligent drug delivery system according to claim 1, further comprising a memory, wherein the controller is configured to store in the memory the multi-axis motion data and the orientation data received by the controller.

3. The intelligent drug delivery system according to claim 2, wherein the controller continually stores records of positional locations and/or multi-axial positional movements of the device body in the memory as recorded movement data.

4. The intelligent drug delivery system according to claim 3, wherein the recorded multi-axis movement data is associated with relevant metadata.

5. The intelligent drug delivery system according to claim 4, wherein the metadata comprises information about the brand and/or the type of the pharmacological drug.

6. The intelligent drug delivery system according to claim 5, wherein the metadata comprises information about the strength of the pharmacological drug.

7. The intelligent drug delivery system according to claim 4, wherein the data is analyzed to determine the state of a lifestyle activity level of the user or an indication or determination as to whether the user is awake or asleep.

8. The intelligent drug delivery system according to claim 3, wherein the recorded movement data is linked to metadata information, and wherein the metadata information comprises a calculated level of the pharmacological material circulating in the user contemporaneous with the recorded movement data.

9. The intelligent drug delivery system according to claim 3, wherein the recorded movement data and associated metadata is configured to be remotely accessed by a clinician remote computer.

10. The intelligent drug delivery system according to claim 9, wherein the pump instruction signal is configured to be modified by the clinician remote computer.

11. The intelligent drug delivery system according to claim 3, wherein the controller continually stores records the delivery rate and changes to the delivery rate in the memory as drug delivery data.

12. The intelligent drug delivery system according to claim 11, wherein the recorded movement data and the drug delivery data is configured to be remotely accessed by a clinician remote computer.

13. The intelligent drug delivery system according to claim 12, wherein the pump instruction signal is configured to be modified by the clinician remote computer.

14. The intelligent drug delivery system according to claim 1, wherein the controller is configured to generate the pump instruction signal to reduce the delivery rate of the pharmacological material for a predetermined amount of time, wherein the controller is configured to determine whether there are any multi-axial changes in frequency and/or intensity in speed of the device body from previous determinations of frequency and/or intensity in speed of the device body based on the motion data and/or the orientation data, changes in linger times of the device body, and/or changes in multi-axial cadence of movement of the device body during the predetermined amount of time compared to movement recorded prior to the predetermined amount of time, and wherein, if any one or more of the changes are above a predetermined threshold, the controller is configured to generate a new pump instruction signal to restore the delivery rate of the pharmacological material to the delivery rate prior to the reduction of the delivery rate of the pharmacological material.

15. The intelligent drug delivery system according to claim 1, wherein the controller is configured to calculate instant pharmacological circulation levels for a first selected time period and a second, subsequent, selected time period and compare the calculated levels of the second selected time period to the first selected time period, wherein the pump instruction signal is further based on the comparison.

16. The intelligent drug delivery system according to claim 1, wherein the accelerometer sensor is a minimum six-axis accelerometer sensor.

17. The intelligent drug delivery system according to claim 1, further comprising a wrist wearable device body configured to be worn on a wrist of the user, wherein the wrist wearable device body comprises:
a wrist accelerometer sensor arranged in or on the wrist wearable device body and configured to output wrist multi-axis motion data based on detected multi-axis motion and acceleration;
a wrist gyroscopic pitch sensor arranged in or on the wrist wearable device body and configured to output wrist orientation data based on detected orientation;
wherein the controller is configured to generate the pump instruction signal based further on the wrist multi-axis motion data and/or the wrist orientation data, and
wherein the controller is configured to determine whether adjustment to the daily dosage is needed and to adjust the daily dosage in the closed-loop manner in a closed-loop between the wrist sensors arranged in or on the wrist wearable device body, the sensors arranged in or on the device body, and the controller.

18. The intelligent drug delivery system according to claim 17, further comprising a pump arranged in or on the device body, wherein the pump is configured to deliver the pharmacological material to the user.

19. The intelligent drug delivery system according to claim 1, wherein the controller is configured to adjust the delivery rate of a basal rate of delivery of the pharmacological material based on the determined multi-axial movement of the device body, multi-axial speed and acceleration of the device body, the linger times of the device body, and/or the multi-axial cadence of movement of the device body in order to achieve the minimum level of daily dosage of the pharmacological material.

20. The intelligent drug delivery system according to claim 1, wherein the controller is configured to determine the minimum level of daily dosage further based on user historical recorded data that indicates a reaction or lack of reaction to earlier delivery rate changes or suspensions of the pharmacological material for the user.

21. The intelligent drug delivery system according to claim 1, wherein the current physically detected Parkinson's disease symptom intensity level or range of the user is determined by the controller based on the multi-axial motion data and/or orientation data.

22. An intelligent drug delivery system comprising:
a first multi-axial device body and a second multi-axial device body;
a first multi-axial accelerometer sensor arranged in or on the first device body and configured to output first multi-axial motion data based on detected multi-axial motion, and a second multi-axial accelerometer sensor arranged in or on the second device body and configured to output second multi-axial motion data based on detected multi-axial motion;

a first multi-axial gyroscopic pitch sensor arranged in or on the first device body and configured to output first multi-axial orientation data based on detected multi-axial orientation, and a second multi-axial gyroscopic pitch sensor arranged in or on the second device body and configured to output second multi-axial orientation data based on detected multi-axial orientation;

a controller in communication with the first multi-axial accelerometer sensor, the second multi-axial accelerometer sensor, the first multi-axial gyroscopic pitch sensor, and the second multi-axial gyroscopic pitch sensor, the controller being arranged to be worn by a user;

wherein the controller is configured to determine multi-axial positional locations of the first and second multi-axial device bodies, a speed of the first and second multi-axial device bodies, linger times of the first and second device bodies, and/or a cadence of multi-axial movement of the first and second device bodies;

wherein the controller is configured to generate a pump instruction signal based on the first multi-axial motion data, the first multi-axial orientation data, the second multi-axial motion data and/or the second multi-axial orientation data, the pump instruction signal including an instruction to change or suspend a delivery rate of a pharmacological material to achieve a daily dosage of the pharmacological material;

wherein the pharmacological material is configured to treat one or more abnormal movement symptoms of Parkinson's disease; and wherein the controller is configured to autonomously dynamically determine whether adjustment to the daily dosage is needed and autonomously dynamically adjust the daily dosage in a closed-loop manner between the sensors arranged in or on the first multi-axial device body and the second multi-axial device body and the controller, without input of a dosage change, based on a current physically detected Parkinson's disease symptom intensity level or range of the user determined by the controller in order to optimize the daily dosage to achieve a minimum level of the daily dosage consistent with abnormal motion control of the user.

23. The intelligent drug delivery system according to claim 22, wherein the first multi-axial device body comprises a pump configured to deliver the pharmacological material to the user and the second multi-axial device body is configured to be worn on a wrist of the user.

24. The intelligent drug delivery system according to claim 23, further comprising a multi-axis body sensor, configured to be worn on the body of the user.

25. The intelligent drug delivery system according to claim 22, wherein the controller is configured to adjust the delivery rate of a basal rate of delivery of the pharmacological material based on the first multi-axial motion data, the first multi-axial orientation data, the second multi-axial motion data and/or the second multi-axial orientation data in order to achieve the minimum level of daily dosage of the pharmacological material.

26. The intelligent drug delivery system according to claim 22, wherein the controller is configured to determine the minimum level of daily dosage further based on user historical recorded data that indicates a reaction or lack of reaction to earlier delivery rate changes or suspensions of the pharmacological material for the user.

27. The intelligent drug delivery system according to claim 22, wherein the current physically detected Parkinson's disease symptom intensity level or range of the user is determined by the controller based on the multi-axial motion data and/or orientation data.

* * * * *